(12) United States Patent
Margus et al.

(10) Patent No.: US 7,427,480 B2
(45) Date of Patent: Sep. 23, 2008

(54) LIFE SCIENCES BUSINESS SYSTEMS AND METHODS

(75) Inventors: Bradley A Margus, Boca Raton, FL (US); David R Cox, Belmont, CA (US)

(73) Assignee: Perlegen Sciences, Inc., Mountain View, CA (US)

( * ) Notice: Subject to any disclaimer, the term of this patent is extended or adjusted under 35 U.S.C. 154(b) by 386 days.

(21) Appl. No.: 11/181,159

(22) Filed: Jul. 13, 2005

(65) Prior Publication Data

US 2006/0008834 A1 Jan. 12, 2006

Related U.S. Application Data

(63) Continuation-in-part of application No. 10/402,839, filed on Mar. 26, 2003, now Pat. No. 6,955,883, and a continuation-in-part of application No. 10/107,508, filed on Mar. 26, 2002, now Pat. No. 7,135,286.

(51) Int. Cl.
*C12Q 1/68* (2006.01)
(52) U.S. Cl. .............................. 435/6; 702/20
(58) Field of Classification Search ........................ None
See application file for complete search history.

(56) References Cited

U.S. PATENT DOCUMENTS

| | | | |
|---|---|---|---|
| 5,525,464 | A | 6/1996 | Drmanac et al. |
| 5,972,614 | A | 10/1999 | Ruano et al. |
| 2002/0012921 | A1 | 1/2002 | Stanton |

FOREIGN PATENT DOCUMENTS

| | | |
|---|---|---|
| WO | WO 01/01218 A2 | 1/2001 |
| WO | WO 01/04270 A1 | 1/2001 |

OTHER PUBLICATIONS

Jones, P., "The commercialization of bioinformatics," EJB Electronic Journal of Biotechnology, vol. 3 No. 2, 96-113, Aug. 15, 2000.
Roses, A., "Pharmacogenetics and future drug development and delivery," The Lancet, vol. 355, 1358-1361, Apr. 15, 2000.
Goddard, K., et al, "Linkage Disequilibrium and Allele-Frequency Distributions for 114 Sing-Nucleotid Polymorphisms in Five Populations," The American Journal of Human Genetics, 66:216-234, 2000.
Toivonen, H. et al, "Data Mining Applied to Linkage Disequilibrium Mapping," The American Journal of Human Genetics, 67:133-145, 2000.
The World of Pharmacia Biotech '95, "Squencing Kit," p. 177, Copyright 1994.
Patil, N., et al, "Blocks of Limited Haplotype Diversity Revealed by High-Resolution Scanning of Human Chromosome 21," Science Magazine 294, 1719-1723 (2001).
Daly, M., et al., "High-resolutio nhaplotype structure in the human genome," Nature Genetics vol. 29, 229-232 (2001).
Oestreicher, P., "4th Annual Pharmacogenomics and Medicine Lectures," Pharmacogenomics (2001) 2(3):291-296.
Form 10-K filed by Millennium Pharmaceuticals for the fye Dec. 31, 2000.
Form 10-K filed by Applera Corp for the fye Jun. 30, 2001.
Form 10-K filed by Genzyme Corp for the fye Dec. 31, 2000.
Form 10-K filed by Human Genome Sciences, Inc. for the fye Dec. 31, 2000.
Form 10-K filed by Genaissance Pharmaceuticals, Inc. for the fye Dec. 31, 2000.
Perlegen Sciences, Inc. Private Placement Memorandum dated Mar. 30, 2001.
San Jose Mercury News article entitled, "Gene Hunters," dated Jan. 21, 2002.
Barcellos, L., et al, "Association Mapping of Disease Loci, by Use of a Pooled DNA Genomic Screen," The American Journal of Human Genetics, 61:734-747, 1997.

*Primary Examiner*—James Martinell
(74) *Attorney, Agent, or Firm*—Deana A. Arnold

(57) ABSTRACT

Improved life sciences business systems and methods are disclosed. One or more genomes are scanned for single nucleotide polymorphisms. The polymorphisms are assigned to haplotype blocks, and representative SNPs from the haplotype blocks are used in association studies for pharmaceutical and diagnostic developments.

25 Claims, 2 Drawing Sheets

SEQUENCE LISTING

<160> NUMBER OF SEQ ID NOS: 2

<210> SEQ ID NO 1
<211> LENGTH: 23
<212> TYPE: DNA
<213> ORGANISM: Homo sapiens

<400> SEQUENCE: 1
cgatctgagc gccccttaac ttc                                          23

<210> SEQ ID NO 2
<211> LENGTH: 23
<212> TYPE: DNA
<213> ORGANISM: Homo sapiens

<400> SEQUENCE: 2
tgacctgggc gacctttgac gtg                                          23

LIFE SCIENCES BUSINESS SYSTEMS AND METHODS

CROSS-REFERENCE TO RELATED APPLICATIONS

The present application claims priority to and is a continuation-in-part of U. S. patent application Ser. No. 10/107,508, filed Mar. 26, 2002, entitled "Pharmaceutical and diagnostic business systems and methods," now U.S. Pat. No. 7,135,286; and U.S. patent application Ser. No. 10/402,839, filed Mar. 26, 2003, entitled "Life Sciences Business Systems and Methods" (a continuation-in-part of U.S. patent application Ser. No. 10/107,508 filed Mar. 26, 2002, now U.S. Pat. No. 7,135,286), now U.S. Pat. No. 6,955,883, the disclosures of which are specifically incorporated herein by reference in their entireties for all purposes.

BACKGROUND

Biotechnology/biopharmaceutical companies have found significant commercial success in business methods wherein a biotechnology company partners with a large pharmaceutical company in pursuit of a particular scientific discovery. For example, it is common for biotechnology companies to engage in various discovery processes (e.g. drug "target" discovery processes) whereby they retain downstream intellectual property rights and/or royalty streams. It is also common for biopharmaceutical companies to collaborate with pharmaceutical companies for purposes of drug discovery, wherein the biopharmaceutical companies use one of several methods to identify regions of the genome that play a role in a particular disease.

The progress of a drug from the point it is discovered in the laboratory to its launch in the marketplace, if successful, is referred to as the "drug development pipeline." On average, such a process takes 10-15 years and about $359 million, and it is estimated that only about one in up to several thousand compounds that enter preclinical testing ultimately makes it to the market as a pharmaceutical. In the U.S. a drug pipeline generally comprises eight stages. The first is discovery, in which a candidate compound is synthesized, isolated, and characterized. Next, biological testing is performed as an initial screening for potential activity, toxicity and stability. Preclinical or animal testing follows and includes an extensive series of in vivo and in vitro studies to evaluate safety and biological activity against the targeted phenotype (e.g., disease, susceptibility, etc.) Once it is determined that human trials are warranted, an IND (Investigational New Drug application) filing is submitted to the Food and Drug Administration (FDA). If approved, a Phase I study is performed in which the drug is administered to a small number (~20-80) of healthy volunteers to determine safe dosage ranges, absorption and metabolism of the compound. Following a successful Phase I study, a Phase II study is performed to evaluate the efficacy and adverse events in approximately 100-300 volunteers with the targeted phenotype. Finally, a Phase III study is performed to further evaluate the efficacy and long-term adverse events in approximately 1,000-3,000 volunteers with the targeted phenotype. If the compound "passes" the Phase III study, then preregistration of the compound takes place through the filing of an NDA (New Drug Application) with the FDA. The FDA reviews the research findings and other scientific information contained within the NDA and determines whether or not to approve the drug, and at what dosage and for what specific indication(s) it is to be used, thereby "registering" the drug. The final stage in the drug pipeline is the post-marketing stage in which any adverse reactions or quality control issues are reported to the FDA. The FDA may also require Phase IV studies. Even at this stage, the drug may be recalled or withdrawn from the market. Only about one out of every five drugs that enters clinical trials is approved for patient use. Failure at the end of a clinical trial could nullify many years of work and millions of dollars spent by a research institution or pharmaceutical company.

The DNA that makes up human chromosomes provides the instructions that direct the production of all proteins in the body. These proteins carry out vital functions of life. Variations in DNA are directly related to almost all human diseases, including infectious diseases, cancers, inherited disorders, and autoimmune disorders. Variations in DNA contributing to a phenotypic change, such as a disease or a disorder, may be, e.g., a single variation that disrupts the complex interactions of several genes, any number of mutations within a single gene, any number of mutations in a plurality of loci in the genome, or a combination thereof. For example, Type I and II diabetes have been linked to multiple genes, each with its own pattern of mutations. In contrast, cystic fibrosis can be caused by any one of over 300 different mutations in a single gene. Phenotypic changes may also result from variations in non-coding regions of the genome. For example, a single nucleotide variation in a regulatory region can upregulate or downregulate gene expression or otherwise alter gene activity.

Recent technological developments in the field of human genomics have enabled the development of pharmacogenomics, the use of human DNA sequence variability in the development and prescription of drugs. Pharmacogenomics is based on the correlation or association between a given genotype and a resulting phenotype. Since the first correlation study over half-a-century ago linking adverse drug response with amino acid variations in two drug-metabolizing enzymes (plasma cholinesterase and glucose-6-phosphate dehydrogenase), other correlation studies have linked sequence polymorphisms within drug metabolism enzymes, drug targets and drug transporters with compromised levels of drug efficacy or safety.

Pharmacogenomic data is especially useful in clinical settings where correlation information is used to prevent drug toxicities. For example, patients are often screened for genetic differences in the thiopurine methyltransferase gene that cause decreased metabolism of 6-mercaptopurine or azathiopurine. However, only a small percentage of observed drug toxicities have been explained adequately by the set of pharmacogenomic markers available to date. In addition, "outlier" individuals, or individuals experiencing unanticipated effects in clinical trials (when administered drugs that have previously been demonstrated to be both safe and efficacious), cause substantial delays in obtaining FDA drug approval and may even cause certain drugs to come off market, though such drugs may be efficacious for a majority of recipients.

The various biotechnological methods used to date to identify target genomic regions include, for example, differential gene expression which essentially looks for differences in gene expression between control and case samples; protein-protein interaction maps which are used to identify drug receptors and their immediate effectors; and mining human sequence databases for sequences similar to known disease-related, pharmacokinetic or pharmacodynamic regulators. In comparison, association studies that correlate and validate genomic regions with a particular phenotypic trait rely on population genetics and robust statistical metrics. Association studies provide a powerful tool to obtain greater amounts of information in a shorter amount of time thus reducing costs of research and development efforts.

Because all humans are 99.9% identical in their genetic makeup, the DNA sequence of any two individuals is nearly identical. Variations between individuals include, for example, deletions or insertions of DNA sequences, variations in the number of repetitive DNA elements in non-coding regions and changes in a single nitrogenous base position, or "single nucleotide polymorphisms" (SNP). It is estimated that there are ~7 million common SNPs that have a minor allele frequency of at least 0.1 (i.e., the minor allele of the SNP occurs in at least 10 percent of people). These common SNPs do not occur independently but are inherited from generation to generation in tandem with other SNPs, forming patterns across the genome. Such groups of SNPs (including the genomic region in which they lie) are referred to as SNP haplotype blocks, herein.

Common SNPs are useful for conducting whole-genome association studies. Whole genomes of individuals with and without a phenotypic trait of interest (e.g., resistance to a disease, toxicity from a drug) are scanned and a correlation (or "association") is made between the SNPs and the phenotypic trait. Such whole-genome analyses provide a fine degree of genetic mapping and can pinpoint specific regions of linkage. Methods for whole genome analysis are described in, e.g., U.S. Ser. No. 60/327,006, filed Oct. 5, 2001, entitled "Identifying Human SNP Haplotypes, Informative SNPs and Uses Thereof," assigned to the assignee of the present invention and U.S. Ser. No. 10/106,097, filed Mar. 26, 2002, now U.S. Pat. No. 6,969,586, entitled "Methods For Genomic Analysis", both incorporated herein by reference for all purposes. Further, the identity of SNPs and SNP haplotype blocks across one representative chromosome, e.g. Chromosome 21, are disclosed in U.S. Ser. No., 60/323,059, filed Sep. 18, 2001, entitled "Human Genomic Polymorphisms" assigned to the assignee of the present invention and U.S. Ser. No. 10/284,444, filed Oct. 31, 2002, entitled "Human Genomic Polymorphisms", incorporated herein by reference for all purposes. See also Patil, N. et al, "Blocks of Limited Haplotype Diversity Revealed by High-Resolution Scanning of Human Chromosome 21" *Science* 294, 1719-1723 (2001), disclosing SNPs and haplotype structure of Chromosome 21.

Genomic studies may be used to discover genetic variation between different organisms, for example, bacterial strains. This knowledge could be valuable in identifying the source of an outbreak, whether natural or as a result of bioterrorism. When a bioterror attack occurs, it is important to quickly identify the agent, find its source and apprehend the perpetrators. Similarly, prompt identification of the source of natural, food-borne disease outbreaks can limit the number of affected individuals, thereby saving lives. As such, tools are needed to rapidly and uniquely identify different organism's, such as bacterial strains.

BRIEF SUMMARY

Improved business methods, devices, and systems for utilizing genetic information are provided.

According to one embodiment of the invention, a business method is disclosed that comprises the steps of scanning the human genome for single nucleotide polymorphisms found in regions extending across more than 10,000,000 bases including both genic and non-genic regions; grouping the single nucleotide polymorphisms into haplotype blocks; determining haplotype patterns for each haplotype block; using the SNPs, haplotype blocks and/or haplotype patterns in association studies with a phenotypic trait of interest; using associations in a discovery process; and marketing products from the discovery process.

According to a further embodiment of the invention, a business method is disclosed that comprises the steps of identifying genetic variations in a plurality of strains of an organism; identifying at least one genetic variation that is in linkage disequilibrium with at least one other genetic variation; and determining an association between the genetic variation that is in linkage disequilibrium with at least one other genetic variation and at least one strain of the organism. In some aspects, the organism is an animal, a plant, a microorganism or a virus. In another aspect, the method further comprises collaboration with a partner, which may provide funding or genetic samples for one or more steps in the method. In further aspects, the number of strains analyzed is at least about two, 10 or 50.

According to another embodiment of the invention, a business method is disclosed that comprises the steps of identifying genetic variations in a plurality of strains of an organism; identifying at least one genetic variation that is in linkage disequilibrium with at least one other genetic variation; determining an association between the genetic variation that is in linkage disequilibrium with at least one other genetic variation and at least one strain of the organism; and using the association to identify an isolated strain of the organism. In some aspects, the isolated strain is an unknown pathogen or a hazardous contamination, e.g., related to bioterrorism. In another aspect the method comprises collaboration with a partner. In another aspect, the methods comprise computing allele frequencies for genetic variations and determining which genetic variations distinguish between different strains based on their allele frequencies in those strains. In another aspect, the number of genetic variations analyzed is at least about two, 1000 or 10,000.

According to another embodiment of the invention, a business method for obtaining expedited regulatory review of a drug is disclosed that comprises the steps of identifying genetic variations in a plurality of individuals; identifying at least one genetic variation that is in linkage disequilibrium with at least one other genetic variation; determining an association between the genetic variation that is in linkage disequilibrium with at least one other genetic variation and a response to the drug; using the association to determine whether a patient would benefit from administration of the drug; and combining information from prior regulatory filings for the drug in combination with information from the association to support a new drug approval regulatory filing. In some aspects, the prior regulatory filings were filed in the United States, and in other aspects they were filed abroad. In another aspect, the methods further comprise marketing the drug with a diagnostic test that stratifies a patient population (e.g., a human patient population) so that the subset of the population most likely to benefit from treatment with the drug is identified. In other aspects, the association is determined without a prior hypothesis that a particular genetic region is associated with the drug response.

According to yet another embodiment of the invention, a business method is disclosed that comprises the steps of identifying genetic variations in a plurality of individuals; identifying at least one genetic variation that is in linkage disequilibrium with at least one other genetic variation; attaining an in-licensed drug; reformulating the in-licensed drug to produce a reformulated drug, which is a novel composition; determining an association between the genetic variation that is in linkage disequilibrium with at least one other genetic variation and a response to the reformulated drug; and using the association to determine whether a patient would benefit from administration of the reformulated drug. In certain aspects, the reformulated drug has a different enantiomeric purity, delivery method, and/or dosage form than the in-licensed drug. In some aspects, the reformulated drug is marketed with a diagnostic test that stratifies a patient population (e.g., a human patient population) so that the subset of the population most likely to benefit from treatment with the reformulated drug is identified. In other aspects, the association is determined without a prior hypothesis that a particular genetic region is associated with a response to the reformulated drug.

DETAILED DESCRIPTION

Figure 1:
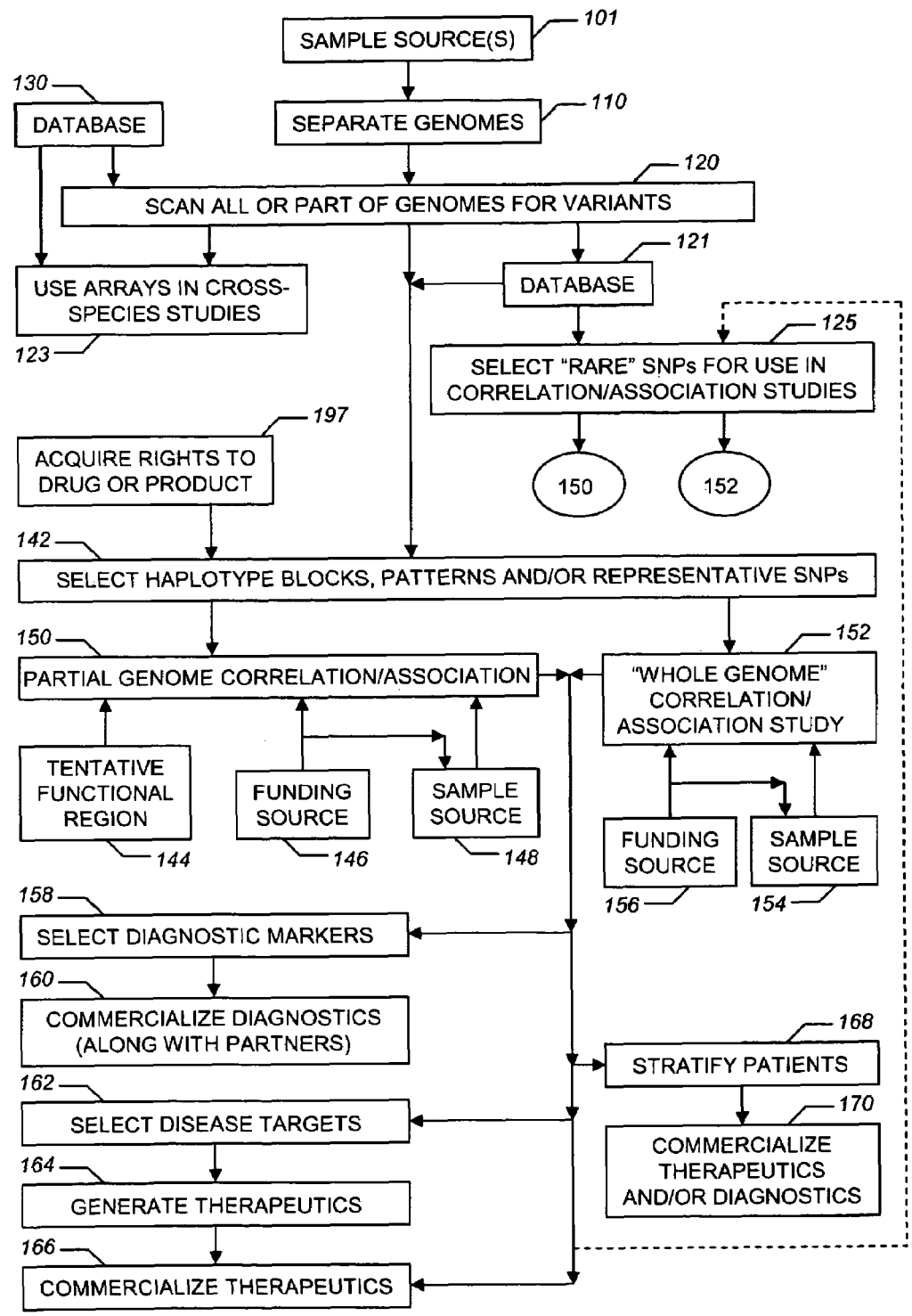
FIG. 1 is a flow chart illustrating certain aspects of the business method herein.

As used in the specification, "a" or "an" means one or more. As used in the claim(s), when used in conjunction with the word "comprising", the words "a" or "an" mean one or more. As used herein, "another" means at least a second or more.

Reference now will be made in detail to various embodiments and particular applications of the invention. While the invention will be described in conjunction with the various embodiments and applications, it will be understood that such embodiments and applications are not intended to limit the invention. On the contrary, the invention is intended to cover alternatives, modifications and equivalents that may be included within the spirit and scope of the invention. Processes that may be used in specific embodiments of the methods herein are described in more detail in the following patent applications, all of which are specifically incorporated herein by reference: U.S. provisional patent application Ser. No. 60/280,530, filed Mar. 30, 2001; U.S. provisional patent application Ser. No. 60/313,264 filed Aug. 17, 2001; U.S. provisional patent application Ser. No. 60/327,006, filed Oct. 5, 2001, all entitled "Identifying Human SNP Haplotypes, Informative SNPs and Uses Thereof"; U.S. provisional patent application Ser. No. 60/332,550, filed Nov. 26, 2002, entitled "Methods for Genomic Analysis"; U.S. patent application Ser. No. 10/106,097, filed Mar. 26, 20026, now U.S. Pat. No. 6,969,589, entitled "Methods for Genomic Analysis"; U.S. patent application Ser. No. 10/236,480, filed Sep. 5, 2002, entitled "Methods for Amplification of Nucleic Acids"; U.S. patent application Ser. No. 10/042,819, filed Jan. 7, 2002, now U.S. Pat. No. 6,897,025, entitled "Genetic Analysis Systems and Methods"; U.S. patent application Ser. No. 10/284,444, filed Oct. 31, 2002, entitled "Human Genomic Polymorphisms"; U.S. patent application Ser. No. 10/448,773, filed May 30, 2003, entitled "Methods for Genomic Analysis"; U.S. patent application Ser. No. 10/286,417, filed Oct. 31, 2002, entitled "Methods for Genomic Analysis"; U.S. patent application Ser. No. 10/426,903, filed Apr. 29, 2003, entitled "Methods for Genomic Analysis"; U.S. patent application Ser. No. 10/768,788, filed Jan. 30, 2004, entitled "Apparatus and Methods for Analyzing and Characterizing Nucleic Acid Sequences"; PCT patent application US04/006693, filed Mar. 4, 2004, entitled "Apparatus and Methods for Analyzing and Characterizing Nucleic Acid Sequences"; U.S. patent application Ser. No. 10/447,685, filed May 28, 2004, entitled "Liver Related Disease Compositions and Methods"; PCT patent application US04/016950, filed May 27, 2004, entitled "Liver Related Disease Compositions and Methods"; U.S. patent application Ser. No. 10/351,973, filed Jan. 27, 2003, entitled "Apparatus and Methods for Determining Individual Genotypes"; U.S. patent application Ser. No. 10/786,475, filed Feb. 24, 2004, entitled "Improvements to Analysis Methods for Individual Genotyping"; U.S. patent application Ser. No. 10/970,761, filed Oct. 20, 2004, entitled "Improved Analysis Methods and Apparatus for Individual Genotyping"; PCT patent application US04/013577, filed Apr. 30, 2004, entitled "Method for Identifying Matched Groups"; U.S. provisional patent application Ser. No. 60/572,533, filed May 18, 2004, entitled "Nonsynonymous Human Genomic Polymorphisms"; U.S. patent application Ser. No. 10/845,316, filed May 12, 2004, entitled "Allele-specific Expression Patterns"; U.S. patent application Ser. No. 10/940,410, filed Sep. 13, 2004, entitled "Methods and Systems for Identifying Predisposition to the Placebo Effect"; U.S. patent application Ser. No. 11/004616, filed Dec. 3, 2004, entitled "Identification of Markers for Strain Classification"; U.S. provisional patent application Ser. No. 60/644,255, filed Jan. 13, 2005, entitled "Use of Alpha 2 Adrenergic Receptor Agonists"; U.S. patent application Ser. No. 10/956,224, filed Sep. 30, 2004, now U.S. Pat. No. 7,127,355, entitled "Methods for Genetic Analysis"; U.S. provisional patent application Ser. No. 60/648,957, filed Jan. 31, 2005, entitled "Compositions and Methods for Treating, Preventing, and Diagnosing Alzheimer's Disease"; U.S. provisional patent application Ser. No. 60/653,672, filed Feb. 16, 2005, entitled "Parkinson's Disease-Related Disease Compositions and Methods"; U.S. patent application Ser. No. 11/058,432, filed Feb. 14, 2005, entitled "Selection Probe Amplification"; U.S. provisional patent application Ser. No. 60/643,006, filed Jan. 11, 2005, entitled "Markers for Metabolic Syndrome Obesity and Insulin Resistance"; U.S. provisional patent application Ser. No. 60/575,495, filed May 27, 2004, entitled "Business Methods for Distribution of Chloroquine Compounds"; and U.S. patent application Ser. No. 11/043,689, filed Jan. 24, 2005, entitled "Associations Using Genotypes and Phenotypes", the disclosures all of which are specifically incorporated herein by reference in their entireties for all purposes.

Throughout this disclosure various patents, patent applications and publications are referenced. Unless otherwise indicated, each is incorporated by reference in its entirety for all purposes. Publications mentioned herein are cited for the purpose of describing and disclosing reagents, methodologies and concepts with the present invention. Nothing herein is to be construed as an admission that these references are prior art in relation to the inventions described herein.

I. General

Scientists have completed several drafts of the genetic sequence of a human being, marking the beginning of a new era in biological research. Although this in itself is a significant accomplishment, much of the business value is in discovering patterns of variation between individuals and correlating specific genomic regions with a phenotypic trait.

Sequencing the human genome has revealed that there is a high degree of homology in genetic information between humans—any two humans share approximately 99.9 percent the same DNA sequence and have the same approximately 20,000 or so genes similarly situated in one of twenty-three chromosomes. However, differences still exist. Approximately 0.1 percent, or one out of every 1,000 DNA letters (i.e., nucleotide bases) is variable, meaning that within the entire human population, some individuals have one nucleotide base at a given position and other individuals have a different nucleotide base at the same position. In fact, single nucleotide polymorphisms (SNPs) account for an estimated of ~7 million common differences (e.g., common SNPs) between individuals and many more rare ones.

Most diseases have a genetic basis that is often the result of numerous genetic factors rather than just one gene. Therefore, when scientists want to understand the genetic causes and resulting biological pathways involved in disorders such as Alzheimer's disease, cancer or asthma, they need to compare the DNA variations of the entire genome of many individuals who have the disease to the genomes of many people who do not have the disease. Once the genetic basis of a disease is discovered, this information can be used to develop diagnostics, prognostics and treatments for the disease.

Further into the drug development and commercialization process, drug companies invest hundreds of millions of dollars to develop a new product, only to suffer large losses due to clinical trial participants having unpredictable effects (e.g., increased toxicity or inadequate or no response to the tested drug). In order to overcome negative results, obtain regulatory approval faster and recoup losses, drug companies need to associate treatment responses with genetic profiles of clinical trial participants. It would be very advantageous for drug companies to be able to predict which individuals in a population will tolerate or respond positively to a tested drug, and/or which individuals will experience negative side effects or no significant improvement from the drug.

By scanning an initial set of genomes, the business methods herein identify common SNPs, haplotype blocks in which "SNPs" occur, and haplotype patterns of SNP alleles. Once these haplotype patterns are known, assays can be used to determine the genetic profiles of many individuals by reading (e.g., genotyping) only a few SNPs from each known haplotype block since SNP alleles within a haplotype pattern are in linkage disequilibrium with one another. In a further embodiment, all SNPs from each known haplotype block may be genotyped and the haplotype patterns determined may be used to ensure data integrity. In other embodiments, SNPs from only a subset of haplotype blocks in the genome may be genotyped. In related embodiments, SNPs are chosen for genotyping based on their ability to predict the genotypes of other SNPs; in such an embodiment, a subset of SNPs is chosen such that the genotypes of that subset of SNPs is predictive of the genotypes of a much greater number of SNPs across the genome (See, e.g., Hinds, et al. (2005) "Whole-Genome Patterns of Common DNA Variation in Three Human Populations", *Science* 307:1072-1079). The results from these assays can be used, directly or indirectly, in drug discovery, clinical trials and other discovery efforts with partners. The results can save partners millions of dollars that would otherwise be spent on unsuccessful clinical trial and fruitless research and development efforts.

The methods presented herein can be performed with or without partners. Partners can include, for example, biotech partners, academic partners, pharmaceutical partners, research institute partners (e.g., private or public, nonprofit or for-profit), veterinary partners, consumer products partners (e.g., in the discovery of shampoos, skin care products and others), agricultural partners, and/or other partners (e.g., scientific partners or government partners), or a combination thereof. Such partners may provide funding for one or more stages or steps of the methods of the invention. For example, partners may provide funding for sample acquisition, sequencing, identification of genetic variations, identification of genetic variations that are in linkage disequilibrium with other genetic variations, genotype or allele frequency comparisons, determination of an association between one or more genetic variations and one or more phenotypes of interest, development of a drug or diagnostic, marketing of a drug or diagnostic, or other financial support. In other aspects, a partner may provide personnel, analysis, software, nucleic acid samples, laboratory space, technology, or other systems, equipment or services useful for the practice of the methods of the invention. In yet another aspect, a partner such as a pharmaceutical partner may provide a small molecule or a class of small molecules for screening and potential utility for treating a certain phenotype. For example, a partner may provide such a small molecule for in-licensing in exchange for, e.g., royalty payments. In another example, a small molecule may be co-developed by the partner and an institution performing pharmacogenomic studies, e.g., the partner could provide the small molecule, previous clinical data, and/or patient samples. Further, analysis of the pharmacogenomic study results could be performed by individuals from either the partner, the institution or both.

The tremendous market advantage obtained by pharmaceutical companies (or other companies) as a result of association studies is one of the bases for the business methods and systems herein. In some cases, instead of evaluating all 3 billion bases from each genome, or even the ~7 million common SNPs, it is possible to evaluate as few as 300,000 to 500,000 SNPs or even less in order to make a correlation with the whole genome of an organism. The haplotype patterns detected by genotyping these particular SNPs provide enough information to allow statistically accurate association data to be extracted from specific populations. Alternatively, if one identifies a large percentage of common SNPs in a genetic region in an association study, the haplotype blocks and patterns may be used to verify genotyping results. Pharmaceutical partners, for example, may then pay for the association of human genetic profiles with disease symptoms, drug responses, or other phenotypic states. Agricultural partners, for example, may pay for the association of genetic profiles of various crops with pest resistance, better quality produce, better yields or other phenotypic states. Veterinary partners will pay for association of genetic profiles of various animals with drug resistance, improved performance, increased virility or other phenotypic traits.

Furthermore, one can acquire the rights to drugs that others place at reduced value (such as those that failed to gain regulatory approval, failed to meet primary efficacy endpoints in late-stage clinical trials, have serious adverse affects, or are not first-line therapy) and apply this technology herein to determine which patients are best suited for the drug; thereby, significantly increasing the drug's value. For example, on Sep. 30, 2004 Merck & Co., Inc. announced a voluntary worldwide withdrawal of VIOXX® (rofecoxib), a highly successful arthritis and acute pain medication. VIOXX® was launched in the United States in 1999 and has been marketed in more than 80 countries with worldwide sales in 2003 at $2.5 billion. Although VIOXX® benefited many patients, it was found to increase an individual's relative risk for confirmed cardiovascular events, such as heart attack or stroke. Pharmacogenomic studies could to identify genetic loci associated with an increased risk of such cardiovascular events. These genetic loci could be used to develop a diagnostic to identify individuals who are likely to experience the adverse event. The diagnostic could be used in combination with the drug, thereby allowing the re-release of the drug for use only by individuals least likely to experience the adverse event. In addition, one can acquire the rights to drugs with prior regulatory filings, and apply the technologies presented herein to gain expedited regulatory approval in the U.S., thereby drastically shortening the time to market as compared to drugs with no previous regulatory filings. Further, one can acquire the rights to new formulations of known drugs and use the methods described herein to gain expedited regulatory approval for the new formulation. In some aspects, gaining regulatory approval for a drug or other treatment comprises determining those individuals who are most likely to have an efficacious response or those who are least likely to experience an adverse event. In some aspects, the prior regulatory filings are in the U.S., and in other aspects the prior regulatory filings are in countries outside of the U.S. In one embodiment, a method for obtaining expedited review of a drug involves identifying and/or genotyping genetic variations in a plurality of individuals (e.g., humans, mice, rats, chimpanzees, or other model organism) and determining an association between the genotypes of one or more of the genetic variations and a response to the drug.

The present methods further contemplate attaining the rights to new formulations of known drugs and gaining regulatory approval for the new formulation. In one embodiment, a method for obtaining review of a reformulated drug involves in-licensing a drug (i.e., the "in-licensed drug"), reformulating the drug to produce a drug that is a novel composition, identifying and/or genotyping genetic variations in a plurality of individuals (e.g., humans, mice, rats, chimpanzees, or other model organism), determining an association between the genotypes of one or more of the genetic variations and a response to the reformulated drug, and using the association to determine whether a patient would benefit from treatment with the reformulated drug. In some aspects, the reformulated drug has a different enantiomeric purity, chiral form, delivery method or dosage form than the in-licensed drug. Examples of delivery methods of include injection, oral administration, implantation, inhalation, insertion or topical application; and examples of dosage forms include tablets, capsules, powders, granules, ointments, solutions, suspensions, patches, suppositories, injections, inhalants, aerosols, gels, and microspheres. Alternatively or in addition, the dosage form of the reformulated drug may contain a different amount of one or more active or inactive ingredients than does the in-licensed drug, or may cause a different rate of metabolism or absorption of the drug (e.g., sustained-release or controlled-release formulations).

The methods of the present invention may also comprise co-marketing a drug with prior regulatory filings or a reformulated drug with a diagnostic test. Such a diagnostic test stratifies a patient population so that the individuals that are most likely to benefit from treatment with the drug are identified. The patient population is a population of individuals that display characteristics that warrant treatment, and these characteristics may include, e.g., their personal medical history, family medical history, or a particular phenotype that they exhibit. For example, they may have been diagnosed with a condition or disease, laboratory tests may indicate that they are at risk of developing a condition or disease, they may have a family history of a genetic disorder, or they may have a personal medical history of adverse or efficacious drug response. The clinician must then determine which treatment from a plurality of treatments is most suitable to treat these patients. The diagnostic test would provide valuable information to the clinician about the likelihood that an individual will benefit from treatment with the drug. For example, if an individual's genotype indicates that they will have an efficacious response with no adverse events, treatment with the drug may be recommended, but if the genotype is indicative of a severe adverse event, treatment with the drug is counter-indicated.

In practicing the methods of the invention, typically, at least about 200, 600, or 900 individuals are genotyped, a portion of which would comprise a "case group" exhibiting a particular drug response, and the rest of which would comprise a "control group" not exhibiting the particular drug response. Any associations found can be used in further individuals (e.g., patients requiring treatment) to determine which would be most likely to benefit from treatment with the drug, and this information could be combined with data from the prior regulatory filings to support a new drug approval regulatory filing. In some aspects, the genetic variations are further analyzed to determine which are in linkage disequilibrium with each other. These may lie within, for example, haplotype blocks or may be grouped into linkage disequilibrium bins (for related methods, see Patil, et al. (supra) and Hinds, et al. 2005 "Whole-Genome Patterns of Common DNA Variation in Three Human Populations", Science 307, 1072-1079.) In certain aspects, only those genetic variations in linkage disequilibrium with at least one other of the genetic variations are analyzed to determine which distinguish between the strains. Responses to drugs that may be associated with the genotypes of genetic variants include, but are not limited to, adverse events (e.g., allergic reactions, cardiac arrhythmia, stroke, bronchospasm, gastrointestinal disturbances, fainting, impotency, rashes, fever, muscle pain, headaches, nausea, birth defects, hot flashes, mood changes, dizziness, agitation, vomiting, sleep disturbance, somnolence, insomnia, addiction to the drug, and death), high efficacy, low efficacy, a placebo effect, or a combination thereof. In general, those individuals who benefit from treatment with the drug are those do not experience severe adverse events and who experience a positive change in symptoms (e.g., cancer remission, nerve damage reversal, pain reduction, increased motor control, memory, energy, etc.—essentially any positive physical or mental response to the treatment); and those patients who do not benefit from treatment are those that do experience unacceptable or severe adverse events and/or who do not experience a positive change in symptoms. Methods for determining an individual's risk of having an adverse event or efficacious response, which may be used with the methods described herein, are detailed in U.S. patent applications 60/566,302, filed Apr. 28, 2004; 60/590,534, filed Jul. 22, 2004; and Ser. No. 10/956,224, filed Sep. 30, 2004, now U.S. Pat. No. 7,127,355, all of which are entitled "Methods for Genetic Analysis". The methods further provide that the determination of such associations may be performed with our without a prior hypothesis that a particular genetic region or variation is associated with a response to the drug.

With initial funding from partners and/or others, the present methods provide for a comparison of genomic sequences of different species (e.g., human DNA with the DNA of various animals and/or other organisms) to identify evolutionarily conserved sequences, which often correspond to functional genomic regions. Such sequences may be in non-genic regions of DNA, or may occur within genes. Methods for performing such cross-species analysis is described in U.S. patent application Ser. No. 09/972,595, filed Oct. 5, 2001, now U.S. and Ser. No. 10/142,364, filed May 8, 2002. The results of such analysis may be further used to conduct discovery processes with or without partners for development of an internal diagnostic and/or drug pipeline of products.

The present method provides for a resequencing of genomic DNA from species from which an initial draft of the genomic sequence is available. Such a resequencing would provide genomic positions and alleles for polymorphisms (e.g., SNPs) across the genome of the organism. Discovery of polymorphisms in a plurality of species can provide information about their evolutionary divergence and phylogenetic relationships. This information could also be used to conduct discovery processes with or without partners for development of commercial products. The organism may be of a particular taxonomic classification (e.g., subspecies, species, genus, etc.) so that the polymorphisms may be used to distinguish between different strains within that taxonomic classification. For example, if the organism is of a particular species, then the polymorphisms may be used to study the genetic variations that distinguish the different strains of that species from one another. This information could then be used to identify isolated strains. In certain embodiments, the organism is an animal (e.g., of the genus *Homo, Pan, Saimiri, Canis, Felis, Bovis, Rattus, Mus, Tetrahymena*, etc.), a plant (e.g., of the genus *Arabidopsis, Triticum, Phaseolus, Cannabis, Oryza, Zea, Solanum*, etc.), a microorganism (e.g., of the genus *Yersinia, Pneumococcus, Streptococcus, Anthrax, Haemophilus, Salmonella, Staphlylococcus, Escherichia, Candida, Hepatitis*, etc.), or a virus (e.g., human immunodeficiency virus (HIV), hepatitis A, hepatitis B, hepatitis C, influenza, rhinovirus, rotavirus, adenovirus, human T cell lymphotropic virus, herpes, human papilloma virus, etc.). For example, the organism may be a pathogen (e.g., HIV, *Salmonella*, etc.), and the information is used to differentiate between subspecies or strains of the microorganisms, to develop vaccines to prevent infection, or to develop or determine treatments for individuals who are already infected. The development of vaccines or treatment decisions may also depend on clinical knowledge of the strain identified as infecting the individual. In other embodiments, the organism is a hazardous contamination, such as a bioterrorism agent (e.g., anthrax), and the information generated by the methods herein is used to track the source of the agent or to develop treatments for individuals exposed to the agent. (See, e.g U.S. patent application Ser. No. 11/004616, filed Dec. 3, 2004.

In one such embodiment, genomic DNA from a plurality of strains (e.g., at least 2, 5, 10, 20, 50, 100, 500, or 1000 strains) of an organism is sequenced and the resultant DNA sequences are compared to identify positions in the genome that are variable between species ("genetic variations"). Such comparisons are routinely performed and are described, for example, in Patil et al. (2002) "Blocks of Limited Haplotype Diversity Revealed by High-Resolution Scanning of Human Chromosome 21", *Science* 294, 1719-1723. In some aspects, the genetic variations are further analyzed to determine which are in linkage disequilibrium with each other. These may lie within, for example, haplotype blocks or may be grouped into linkage disequilibrium bins. Once the genomic positions that vary between strains are identified, the genotypes at these positions in each strain are catalogued and analyzed to determine which genotypes are indicative of which strain. In certain aspects, only those genetic variations in linkage disequilibrium with at least one other of the genetic variations are analyzed to determine which distinguish between the strains. In some embodiments, this method is performed in collaboration with one or more partners. For example, partners and/or others may provide funding for one or more stages of such a study, including the sample acquisition, initial sequencing, identification of genetic variations, identification of genetic variations that are in linkage disequilibrium with other genetic variations, genotype or allele frequency comparisons, or determination of an association between one or more genetic variations and one or more strains of the organism. Partners may also, e.g., provide nucleic acid samples containing the genetic variations in a plurality of strains of the organism, or may participate in analysis of the sequencing, linkage disequilibrium or association data generated.

In some embodiments of the methods presented herein an association between one or more genetic variations and a particular strain of an organism involves genotyping all or a subset of the genetic variations identified in the plurality of strains to generate a set of genotypes for each variation genotyped that comprises the genotype of the genetic variation in each strain. The genotypes that distinguish between strains are determined by comparing the genotypes for each strain at each genetic variation. For example, if strains A and B are being compared and strain A has a "G" at SNP1 and strain B has a "C" at SNP1, SNP1 distinguishes between strains A and B, the "G" genotype is associated with strain A and the "C" genotype is associated with strain B. Alternatively, if both strains have a "T" and SNP2, SNP2 does not distinguish between strain A and strain B. Further, genotypes at a plurality of genetic variations can be used to distinguish between a set of strains. For example, strains C, D and E are being compared and strain C has a "G" at SNP1, a "T" at SNP2, and a "T" and SNP3; strain D has a "G" at SNP1, a "T" at SNP2, and a "C" and SNP3; and strain C has a "C" at SNP1, a "T" at SNP2, and a "T" and SNP3. In this example, SNP1 distinguishes strain E from strains C and D; SNP2 does not distinguish between strains C, D and E; and SNP3 distinguishes strain D from strains C and E. Therefore, a strain with a "G" at SNP 1 and a "T" at SNP3 is identified as strain C; a strain with a "G" at SNP1 and a "C" at SNP3 is identified as strain D; and a strain with a "C" at SNP1 and a "T" at SNP3 is identified as strain E. The number of genetic variations examined is at least about 2, 10, 50, 100, 500, 1000, 5000, 10,000, 50,000 or 100,000. Methods for determining an association by performing an association study are further described below.

In one particular example, genetic variation between strains of *Salmonella* is used to identify the source of a *Salmonella* outbreak. Over 2,000 strains of *Salmonella* are capable of causing disease in humans, such as food poisoning and typhoid fever. The growing incidence of infections involving drug-resistant strains of *Salmonella* has raised concerns over the impact of *Salmonella* in a bioterrorist attack. When an outbreak occurs, it is important to quickly identify the agent and its source in order to limit the number of affected individuals, determine appropriate treatments for those infected, and apprehend and prosecute the perpetrators if the outbreak was the result of an act of bioterrorism. By comprehensively identifying positions of variation between different *Salmonella* strains, "signature SNPs" can be identified and used to "fingerprint" different strains. In the event of an outbreak, DNA fingerprints from strains infecting individuals can be compared to those of strains associated with suspect sources of contamination, thereby identifying the source of the outbreak. This same approach is applicable to a wide variety of microbial organisms, pathogens and bioterrorism agents. The results of these studies may be used to gain insight into the biology of the organisms, as well.

II. Scientific Basis

The human body contains about 100 trillion cells. Inside each cell is a center called a nucleus. Inside the nucleus are two sets of twenty-three human chromosomes that contain genetic material. One set of chromosomes is inherited from the mother and the other from the father. Each set includes similar genetic information in similar chromosomal locations.

In practice, however, there are subtle differences between paternal and maternal versions of each genome. In fact, except for identical twins, every individual's genome has millions of subtle differences from other individual genomes.

These subtle differences account for most of the differences between individuals, for example, eye and skin color. In addition, they can be used to determine an individual's predisposition to diseases, response to drugs, reaction to the environment, and even in some cases, behavior.

The human genome is gigantic. It is often compared to a book written in a four-letter alphabet using a total of three billion letters, or about one billion words. This makes one person's genome as long as 800 Bibles. If one were to read the genome out loud at the rate of one word per second on eight-hour shifts daily, it would take about a century. It is an immense document, yet it fits inside the microscopic nucleus of a tiny cell that fits easily upon the point of a pin.

Just like a book, the human genome is written in linear, one-dimensional form and is defined by a code that transliterates the four-letter alphabet into a large lexicon of meanings through the order of their groupings. However, whereas English books are written in words of variable lengths using twenty-six letters, genomes are written primarily in three-letter words, using only four letters: adenine, cytosine, guanine and thymine (or in shorthand, A, C, G and T, respectively). Furthermore, instead of being written on flat pages, they are written in long chains or polymers of alternating phosphate and deoxyribose sugar to which the letters or "bases" are attached as side rings. Each human chromosome includes a condensed double helix DNA polymer comprised of complementary DNA polymer strands.

An individual's genomic DNA affects numerous facets of life by providing, for example, the instructions that direct the production of the vast majority RNAs and proteins in the body. Misspellings or "mutations" in DNA may produce mistakes in the regulatory elements of cells, or within proteins and/or RNAs that are produced by cells, thus affecting the normal function of the cells. Although the environment often plays a significant role, variations or mutations in DNA are directly related to almost all human diseases, including infectious diseases, cancers, inherited disorders, and autoimmune disorders. Variations in DNA are also responsible for certain "protective" traits, such as a stronger immune system, more rapid clearing of toxins from the organism, or extended lifespan. Being able to compare the DNA of many individuals and associating those variations to clinical phenotypes (e.g., symptoms, drug response, disease susceptibility or resistance) provides a powerful tool for understanding, diagnosis and treatment of a disease or promotion of a health state.

Knowledge of human genetics has led to the realization that many diseases result from either complex interactions of several genes and/or their gene products, from any number of variations within one gene and its resulting gene product, from any number of variations within a plurality of genes and their resulting gene products, from any number of variations within the non-coding regulatory regions of genes, or from any combination thereof. For example, Type I and II diabetes have been linked to multiple genes, each with its own pattern of variations.

The complexity of the genetic basis of disease highlights the need for new technology capable of looking across the entire genome to analyze large numbers of variations. Scanning entire genomes, or genomic DNA or derivatives thereof (RNA, cDNA, etc.), is one aspect of the business systems and methods disclosed herein.

One embodiment of the implementation of the systems and methods disclosed herein provides for the separation of the full sets of chromosomes from individuals (such as more than 10, preferably more than 20, more preferably more than 25 and even more preferably more than 50 individual genomes) such that there are multiple unique genomes. Preferably, haploid genomes (or genomes derived from a single set of chromosomes) are used. Techniques for employing haploid genomes are disclosed in U.S. Ser. No. 10/106,097, now U.S. Pat. No. 6,969,589. The bases of all or a significant part of these genomes are then scanned or sequenced using, for example, conventional DNA sequencers or chip-based technologies. In a preferred embodiment, whole-wafer technology from Affymetrix, Inc. of Santa Clara, Calif. is used to read each of the genomes at single-base resolution. DNA sequence data generated from each genome is then compared with the other genomes in order to discover all or many of the variations among the genomes. For example, individual 2 in Table I below has two variations as compared with individuals 1 and 3:

TABLE I

| Individual 1: | T | A | G | T | C | G |
| Individual 2: | T | A | A | T | C | C |
| Individual 3: | T | A | G | T | C | G |

Although all humans are approximately 99.9% similar in their genetic makeup (i.e., most of the letters, or bases, of their genomes are identical), there are sequence differences or variations between any two individuals except identical twins. For example, single nucleotide polymorphisms ("SNPs") are single base positions in the genome that are variable in a population of individuals. Typically, each SNP has two forms or "alleles". So, for a haploid population, a portion of the population possesses one of the alleles and the remainder of the population possesses the other allele; and for a diploid population, a first portion of the population possesses two copies of one of the alleles, a second portion of the population possesses two copies of the other allele, and the remainder of the population possess one of each allele. By genotyping (sometimes referred to as, e.g., "scanning" or "reading") a SNP in an individual, one determines the allele(s) present for that SNP in that individual. The allele that is more common is generally referred to as the major allele, and the less common allele, the minor allele. Reference to minor allele frequency refers to the abundance of the minor allele in a given population. For example, take a situation in which ten diploid individuals are genotyped to determine which alleles they possess at a SNP locus on chromosome 2, and 5 individuals are found to be homozygous for allele 1, two individuals are found to be homozygous for allele 2, and the remaining individuals (3) are found to be heterozygous. In such a situation, there would be 20 alleles total, two for each individual. The total incidence of allele 1 is $5(2)+3=13$; and the total incidence of allele 2 is $2(2)+3=7$ (note that $13+7=20$). Thus, since allele two is less abundant it is the minor allele, and the minor allele frequency for that SNP in that group of individuals would be $7/20=0.35$, or 35%. "Common" variations are defined in some cases as those variations (e.g., SNPs) that have a minor allele frequency of at least 0.1 or 10%, although they may also be defined using other minor allele frequency thresholds, such as, e.g., at least about 2% or at least about 5% or at least about 7%.

SNPs are typically found in variable-length blocks ("haplotype blocks") that define a set of SNP positions that are genetically linked (i.e., in linkage disequilibrium with one another). Thus, most alleles at SNPs in a haplotype block do not assort independently from one another, but are passed from generation to generation as haplotype patterns, Put another way, a set of SNP genotypes/alleles for a SNP haplotype block on a single DNA strand constitutes a haplotype pattern. Typically, SNPs used to define a haplotype block are common SNPs, and usually are consecutive common SNPs along a DNA strand. Methods for determining haplotype blocks and patterns are provided, e.g., in U.S. patent application Ser. No. 10/106,097, now U.S. Pat. No. 6,969,589, filed Mar. 26, 2002; U.S. patent application Ser. No. 10/284,444, filed Oct. 31, 2002; U.S. patent application Ser. No. 10/467,558, filed Feb. 14, 2003; and Patil, et al. (2002) "Blocks of Limited Haplotype Diversity Revealed by High-Resolution Scanning of Human Chromosome 21" *Science* 294, 1719-1723. SNP alleles and haplotype patterns across the genome form an individual's genetic profile. In scanning a first, for example 20 to 50 genomes, it is possible to identify haplotype blocks in which linked SNPs occur, as well as the alleles and minor allele frequencies for those SNPs, and the haplotype patterns for those haplotype blocks. After identifying these SNPs with their corresponding alleles and haplotype patterns it becomes possible to determine the sequence of further individuals by reading (e.g., genotyping) only one or a few SNPs from each known haplotype block of SNPs as these SNPs are predictive of the genotypes of other SNPs in the haplotype block due to the genetic linkage between SNP alleles within a haplotype block. Such predictive SNPs are termed "informative SNPs".

In another embodiment of the present invention, linkage disequilibrium (LD) mapping is used to group SNPs for use in association studies, rather than or in addition to the grouping of SNPs into haplotype blocks and patterns. SNPs in close proximity to one another are often strongly correlated, but this correlation structure, or LD, is complex and varies from one region of the genome to another, as well as between different populations. After identifying "LD bins" containing linked SNPs, it becomes possible to determine the sequence of further individuals by reading (e.g., genotyping) only one or a few SNPs from each LD bin as these SNPs are predictive of the genotypes of other SNPs in the LD bin. As for haplotype pattern-based methods, such predictive SNPs are termed "informative SNPs". Methods for determination and use of patterns of LD are provided, e.g., in Hinds, et al. (2005) "Whole-Genome Patterns of Common DNA Variation in Three Human Populations", *Science* 307:1072-1079.

The use of informative SNPs has a tremendous advantage in conducting genetic association studies for pharmaceutical partners, because it utilizes a reduced set of specific SNPs that are indicators for the state of the entire genome. Instead of reading all 3 billion bases from each genome, or even the ~7 million common SNPs that may be found, one may read, for example, only 300,000 to 500,000 informative SNPs, once they are discovered. The haplotype patterns seen by reading these particular SNPs allow statistically accurate association data to be extracted from specific clinical populations. Even when not used to generate association study data, haplotype blocks and patterns or LD bins are useful for validating association results. For example, after pooled samples are scanned and correlated with a phenotypic trait, individuals can be genotyped for presence or absence of SNP alleles and/or haplotype patterns that are found to be of potential significance in the pooled analysis. The informative SNPs may also be used to "check" the genotype of other SNPs of the same haplotype block or LD bin.

According to one aspect of the invention, glass wafers on which high-density arrays of nucleic acid probes have been placed are used. Each of these wafers holds, for example, approximately 60 million nucleic acid probes that can be used to recognize longer nucleic acid sequences in a sample. The recognition of sample nucleic acids by the set of nucleic acid probes on the glass wafer takes place through the mechanism of hybridization. When a sample nucleic acid hybridizes with an array of nucleic acid probes, the sample will bind to those probes that are complementary to sample nucleic acid sequence. By evaluating the level of hybridization of different probes to the sample nucleic acid, it is possible to determine whether a known sequence of nucleic acid is present or absent in the sample.

The use of probe arrays or wafers to decipher genetic information involves the following steps: design and manufacture of probe arrays or wafers, preparation of a sample containing target nucleic acids, hybridization of target nucleic acids to the array, detection of hybridization events and data analysis to determine the sequence of the nucleic acids in the sample. The preferred wafers or probe arrays are manufactured using a process adapted from semiconductor manufacturing to achieve cost effectiveness and high quality, as for example, those manufactured by Affymetrix, Inc.

The design of the wafers or nucleic acid probe arrays begins by probe selection. The probe selection algorithms are based on ability to hybridize to the particular nucleic acid sequence to be scanned. With this information, computer algorithms are used to design photolithographic masks for use in manufacturing the probe arrays. Probe arrays are preferably manufactured by light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. In some embodiments of the present invention, multiple probe arrays are synthesized simultaneously on a large glass wafer. This parallel process enhances reproducibility and helps achieve economies of scale. Method for array design and fabrication are well known to those of skill in the art and are provided, e.g., in U.S. Pat. Nos. 5,252,743, 5,405,783, 5,424,186, 5,445,934, 5,510,270, 5,571,639, and 5,837,832.

Once fabricated, the wafers or nucleic acid probe arrays are ready for hybridization. The nucleic acids to be analyzed are isolated, amplified and labeled with a fluorescent reporter group. The labeled nucleic acids are then incubated with the array using a fluidics station and hybridization oven. After the hybridization reaction is complete, the array is inserted into the scanner, where patterns of hybridization are detected. The hybridization data are collected as light emitted from the fluorescent reporter groups already incorporated into the nucleic acids, which are now bound to the probe array. Probes that most closely match (i.e., are most complementary to) the labeled nucleic acids produce stronger signals than those that have mismatches. Since the sequence and position of each probe on the array are known, by complementarity, the sequence of the nucleic acid applied to the probe array can be determined. Methods for hybridization, detection and data analysis are provided, e.g., in U.S. Pat. Nos. 6,300,063 and 6,586,750, as well as in U.S. patent application Ser. No. 10/768,788 (filed Jan. 30, 2004), Ser. No. 10/786,475 (filed Feb. 24, 2004), Ser. No. 10/970,761 (filed Oct. 20, 2004), 60/643,006 (filed Jan. 11, 2005) and 60/648,957 (filed Jan. 1, 2005). Further methods are provided in U.S. patent application Ser. No. 60/653,672, filed Feb. 16, 2005, entitled "Parkinson's Disease-Related Disease Compositions and Methods".

The data and information generated by the scientific assays disclosed is valuable to numerous industries. For example, information concerning potential drug targets is highly valuable to the biotech industry and can greatly speed up the drug discovery process, and hence time-to-market. Similarly, information concerning the effectiveness, safety and efficiency of given drug is extremely valuable to the pharmaceutical industry and can save a company substantial money in lost revenue or research expenses due to failures in clinical trials. The information generated herein may also be valuable to the agricultural industry, defense department, Center for Disease Control, veterinary medicine industry, consumer products industry, insurance and healthcare provider industry and forest management (by providing genetic basis for useful traits in e.g., plants, infectious microorganisms, trees, laboratory animals and domestic animals), for example. Essentially, the data and information generated by the scientific assays disclosed herein is valuable to any industry that can benefit from information linking genetic polymorphisms to phenotypic traits and treatment of phenotypic traits.

III. Business Applications

The drug research and development process includes everything from the discovery of target genomic regions to drug discovery and final product launch. This process is currently very lengthy, expensive and risky. On average, it takes twelve years to develop a product from the initial research laboratory period to FDA approval. Any event that delays the commercialization or development process of a potential drug can cost the affected company a loss of revenue of up to $1 billion annually. Conversely, any change that can accelerate commercialization or development cycle of a potential drug can bring significant financial benefits to the affected company that implements such changes.

Accelerated time-to-market not only brings the benefit of earlier sales revenues but the expanded market share enjoyed by companies that are the first to enter a segment before its competitors. This is critical, because the period of market exclusivity for the first drug in a new market therapeutic class is typically much shorter than would be desirable. Consequently, marketing expenditures have increased rapidly as companies attempt to maintain or increase market share. In addition to the time-to-market factors, the odds of any compound successfully making it through clinical trials and regulatory approval are miniscule due to the combination of long development cycles and high failure rates. Therefore, business systems and methods that improve the efficiency and timeliness of regulatory approval are highly valuable.

Genomic differences have long been recognized as influencing how patients respond to drugs. Historically, however, pharmaceutical companies generally have not considered genomic differences between patients in developing and implementing clinical trials or in the marketing of approved drugs. The methods used by the pharmaceutical industry to develop new drugs and to improve existing drugs may be changed when genetic variations are taken into account. Genetic variations can play a significant role in all stages of pharmaceutical research and development, including e.g. discovery, preclinical testing, clinical trials, and regulatory approval. Genetic variation information can also be used to improve drugs already on the market by providing information to better select drugs for a particular patient, e.g., via patient stratification as described below.

More recently, pharmaceutical companies have recognized the need to improve research and development efficiency by utilizing genomics in their drug discovery programs. This effort is necessary for companies to match historical revenue growth levels and to meet shareholders' expectations. The drive by pharmaceutical companies for efficiency provides an opportunity for application of genome-wide scanning technologies during both the research and clinical development cycle. Specific examples of methods that may be used with the present invention during both the research and clinical development cycle include those described in U.S. patent applications 60/566,302, filed Apr. 28, 2004; 60/590,534, filed Jul. 22, 2004; and Ser. No. 10/956,224, now U.S. Pat. No. 7,127,355, filed Sep. 30, 2004, all of which are entitled "Methods for Genetic Analysis".

One example of the application of the business systems and methods herein can be found in population segmentation or stratification. It is generally acknowledged that most drugs work more effectively for some patients than others. Because this variability in patient response is often poorly understood, pharmaceutical companies may unnecessarily discontinue further drug development, fail to obtain regulatory approvals for promising drug candidates, or if approvals are obtained, be unable to market an approved drug effectively or to obtain approval for third party reimbursement. Often these problems stem from a low overall efficacy of a drug that is highly efficacious in a subpopulation of patients, or from a drug that is highly efficacious, but that displays serious adverse events in a small subset of patients treated. As such, it would be highly valuable for a drug company to be able to stratify a patient population so that only those that will have an efficacious response in the absence of adverse events can be identified for treatment with a given drug or other medical regimen. Thus, individuals unlikely to have an efficacious response or likely to have an adverse event can avoid wasting time and money on a treatment that is unlikely to be a benefit to them.

In one embodiment, methods of the invention comprise correlating genomic variation with drug response in clinical trials to improve the drug development and marketing process. For example, pharmaceutical companies could association study data (e.g., pharmacogenomic data) from earlier stages of clinical trials to make more informed decisions on whether or not to continue trials, whether or not to enter later-phases of trials or which patients to enroll in later-stages (e.g., phase III or IV). For example, enrolling patients with genetic predisposition for positive drug response can improve the therapeutic index for these patients and improve the possibility of regulatory approval. Furthermore, such pharmacogenomic data can enable pharmaceutical companies to improve drug marketing by identifying segments of the population for whom particular drugs are likely to be more effective than other drugs (whether more efficacious or lacking in adverse events or both), and encouraging physicians to preferentially prescribe such drugs to these patients. Marketing to physicians can be accomplished by continuing medical education, publication in peer-reviewed journals, internet or print advertising, or direct sale calls (e.g., in person, by email, or by telephone). In addition, by using the information disclosed herein a company can better market a drug by segregating a responder population from a non-responder population, or by segregating a population that encounters negative side effects (or even toxicity) from a population that does not suffer negative effects. Further, this may allow a company to keep a drug on the market that would otherwise be withdrawn, or to reintroduce a drug that has already been withdrawn due to adverse effects. The information generated can also be used to create diagnostic kits, for example, to identify individuals predicted to have a highly efficacious response or a low probability of adverse events when treated with a given medical intervention (or to identify individuals predicted to respond poorly, either due to low efficacy or adverse effects, so that those individuals may be excluded from treatment.)

Drugs are often developed to interact with a single version of a gene product, e.g., protein or receptor in the human body. These gene products may be involved in, for example, biochemical pathways underlying a disease, drug metabolism, or other phenotypic traits. A drug may therefore, for example, only be effective in individuals that have a particular genetic variation encoding a specific version of a protein or receptor for which the drug was designed. Individuals, who do not have the genetic variation, and therefore do not have the specific version of the protein or receptor for which the drug was designed, may not respond to the drug or may experience adverse side effects, such as increased toxicity for example. Thus, identifying these genetic variations allows the practitioner to predict whether the individual will benefit from treatment with the drug, and therefore whether they should be administered the drug or not.

To further illustrate the difficulties solved herein, some drugs can interact, directly and/or indirectly, with a variety of different proteins that are encoded and regulated by different genomic regions. Therefore, more than one genomic region can determine how an individual responds to a given drug. The inventions herein can be used to identify such multiple regions. Individuals who are candidates for treatment with such a drug can be prescreened to identify their genotypes at these different genomic regions in order to determine the likelihood that they would benefit from treatment with the drug, or whether a different treatment regimen would be more appropriate. As genetic variations are better understood, it is clear that an individual's response to a given drug is dependent upon that individual's unique genome or more specifically variations within the genome.

A practical approach to understanding why different individuals respond differently to the same drug is found in grouping individuals together based upon specific genomic similarities or similar haplotype patterns. These genomic similarities can occur between unrelated individuals from different ethnic groups and/or from different geographic regions. The ability to identify and associate genetic variations with a phenotypic state (e.g., disease and drug responses) across the entire genome can facilitate the entire drug development process and can reduce the time-to-market for therapeutics. For example, genetic profiles of select subsets of patient populations may be used to enable pharmaceutical companies to identify drug targets, focus on potentially better leads and move quicker into screening assays. In addition, better drug targets can also provide for safer, more effective points of therapeutic intervention.

Markets that may be addressed by the business systems and methods disclosed herein include, but are not limited to, evaluation of genetic variations and drug response, evaluation of genetic variations to identify and validate target regions, evaluation of variation and susceptibility (or resistance) to disease, identification of conserved non-coding regions that may contain gene regulatory sequences, evaluation of genetic variations and regulatory regions affecting development, and evaluation of other genotype-phenotype associations with commercial potential, such as in consumer products and agriculture. Potential customers or partners for genome-wide pattern information, conserved region information, patient profiling services and other scientific partnerships include, for example, numerous companies in the pharmaceutical, biotechnology and agricultural industries, as well as academic centers and government research institutes.

Other potential customers or partners for association studies include, for example, healthcare providers, insurance companies, government entities (e.g., Medicaid, Medicare) and employers or any other entity interested in achieving more economical or effective system for providing or paying for medical or life insurance. Such parties can utilize association studies, for example, to selectively approve expensive drugs to patients who are correlated with a susceptibility to an adverse reaction from a generic drug, evaluate better an individual's likelihood to suffer from disease (or die) prior to underwriting them and more effectively selecting health and life insurance premiums for individuals. These parties may provide funding and/or sample sources for the association studies herein.

The business systems and methods herein further comprise, for example, the development of DNA-scanning and wafer technology and use of that technology's genome scanning capabilities for identifying commercially valuable genetic regions through research collaboration, and verifying such results using association studies. Up-front fees, research payments, milestone payments, database subscriptions, product sales and royalties may all contribute revenue to the business model.

In the short-term, the business strategies and methods herein can generate revenues through several means. First, revenue can be generated by providing genomic data obtained and analyzed from large scale scanning of genomes. Such data can further be used, for example, for genotyping and association studies and can further be licensed to biotechnology, pharmaceutical, or other interested parties on a non-exclusive basis. In addition or alternatively, revenue can be generated by entering into discovery contracts on an exclusive or non-exclusive basis with biotech, pharmaceutical, or other companies that are interested in specific areas of the genome, or specific disease areas across portions or all of the genome, even before scanning the first genomes. Any of the methods herein may be used to verify (or remove) existing drug target candidates. Furthermore, the business methods herein can be used to identify SNPs, LD bins, haplotype blocks and/or haplotype patterns in regions conserved with other species. This can be used for cross species studies. Similar methods may also be used to compare subspecies, e.g., strains of bacteria, viral variants, etc.

In the mid-term, the business strategies herein encompass generating revenue through at least five means. This can add or replace other sources of revenue. First, collaboration agreements can be entered into to provide genome-wide sequencing and genetic profiling (association studies) services that enable biotechnology, pharmaceutical and/or other partners to analyze specific populations. The populations may comprise, for example, individuals affected by a particular disease, participants in clinical trials or groups displaying a particular response to a drug or environmental stimulus. Portions of the intellectual property from such efforts may be retained by the company performing such studies. The company performing the studies may then further develop drug targets and/or diagnostic products based on the retained intellectual property. Second, contract and/or grant funding from non-profit grant-giving organizations such as the federal government may be used for either SNP discovery, LD analysis, haplotype block/pattern analysis, or association studies. Third, drugs can be in-licensed where genome-wide association studies are expected to add significant value, and then out-licensed at a premium to other companies or in exchange for substantial milestones and royalties after identification of the genetic basis of, for example, a drug metabolism response or adverse event. Fourth, pharmaceutical partners can contract for research funded by those pharmaceutical partners. Furthermore, as part of an inter-company cross-licensing agreement, chip or other platform suppliers will pay a royalty on sales to its customers of chips or other technologies containing content generated by the business.

In the longer term, royalties from products (e.g., drugs and diagnostics) developed and commercialized can generate revenue. Such products include, for example, products previously in-licensed, products developed and/or commercialized independently using internal pharmaceutical development efforts and products developed in collaboration with partner(s). The association studies linking particular genetic variations and clinical symptoms will be extremely valuable in identifying drug targets as well as optimizing existing therapies. Agreements entered with pharmaceutical and biotechnology companies will include royalty rights on products derived from this data.

Importantly, generated revenue can be used to conduct similar or different internal pharmaceutical development efforts that can potentially lead to the development of commercial products.

IV. Business Flow

FIG. 1 illustrates overall steps in the business systems and methods herein. As shown, at step 101 initial genomic samples are obtained. Samples of clinical population can be obtained from, for example, hospitals, universities, or companies that bank such samples for sale to third parties. Other partners or entities can also provide sample sources. In most embodiments, the sample sources will include genomic DNA or derivatives thereof from human sources although other organisms can be utilized as well. At this stage the samples need not be from sample or control groups. The samples are preferably collected from a diverse group, such as from different ethnic background or different geographic regions. Examples of different ethnic backgrounds include Asian, Middle-Eastern, African, Nordic, South Pacific, etc. Further sub-groups may also be compared.

Once an institution is ready to begin clinical trials, an IND (investigational new drug application) is filed with the FDA (Food and Drug Administration) to begin to test the drug in people. The IND includes information such as results from preclinical studies, where and by whom the new studies will be performed, and the chemical structure, manufacture and biological activity of the drug. A clinical protocol outlining the objectives of the proposed study may also be included in an IND submission. If the FDA does not disapprove the IND within 30 days, it becomes effective, whereby the institution can progress with the clinical trials. Potential investigators (e.g., MDs) who will participate in the study are chosen, and these investigators will submit the clinical protocol and an informed consent form to an institutional review board (IRB) for review and approval. In addition, the clinical protocol and related documents are also reviewed by an IRB where the studies will be conducted, and progress reports on the study will be submitted at least annually to the FDA. After informed consent forms are reviewed and approved by the IRB, but prior to sample collection, potential donors are required to review and provide their consent by signing an informed consent form prior to providing a biological sample for the study. Both the institution and any partner(s) would abide by any and all applicable laws (e.g., local, state and federal) for human sample collection. In general, clinical trials are divided into three phases. Phase I clinical trials test a drug's safety profile, determine a safe dosage range and duration of action for the drug, and determine how the drug is absorbed, distributed, metabolized and excreted; phase II clinical trials assess the drug's effectiveness; and phase III clinical trials are longer term studies that assess the efficacy and any adverse effects of the drug. Following a clinical trial in which a drug demonstrated both safety and effectiveness, an institution may file an NDA (new drug application) with the FDA. Once the FDA approves the NDA, the drug becomes available for physicians to prescribe. The institution that provides the drug continues to submit periodic reports to the FDA, including any cases of adverse reactions and appropriate quality-control records. In some cases, the FDA required additional studies (Phase IV) to evaluate long-term effects.

At step 110 the homologous chromosomes are preferably separated from one another. Such separation utilizes, in a preferred embodiment, somatic cell hybrid technology as described in U.S. Ser. No. 10/106,097, now U.S. Pat. No. 6,969,589, claiming priority to U.S. Ser. No. 60/332,550, filed Nov. 26, 2001, entitled "Methods of Genomic Analysis," incorporated herein by reference for all purposes.

At step 120 the genomes are scanned for variants from a baseline sequence ("reference sequence") in a reference database 130. Variants can include, for example, SNPs or contiguous stretches of genomic DNA (variant DNA stretches) comprising one or more SNPs. Stretches of genomic DNA can comprise of at least 1000 contiguous bases, at least 5,000 contiguous bases, at least 10,000 contiguous bases, at least 50,000 contiguous bases, at least 100,000 contiguous bases or at least 500,000 contiguous bases. Furthermore, variant DNA stretches can comprise of at least 1 SNP, at least 5 SNPs, at least 10 SNPs, at least 25 SNPs, at least 50 SNPs, or at least 100 SNPs. The reference database may be proprietary or a public database such as GenBank. Preferably, more than 10 different sources are scanned (it being understood that a single diploid organism contains the genetic code from two different sources). In more preferred embodiments, more than 20 different sources are scanned, preferably more than 25 different sources, more preferably more than 30 different sources, preferably more than 50 different sources, and more preferably more than 100 sources are scanned. The genomes that are scanned are preferably from genetically diverse groups such as, for example, different racial groups, ethnic groups or geographic locations. This is based on the assumption that evolutionarily older SNPs that have more global applicability are common SNPs. However, specific groups or sub-groups can also be scanned to identify variants that are more useful for those sub-populations. As described in U.S. Ser. No. 10/042,819, now U.S. Pat. No. 6,897,025, entitled "Genetic Analysis Systems and Methods," filed on Jan. 7, 2002, assigned to assignee, the scanning step may be a one-step or two-step process. In a two-step process each consecutive base in a genetic sequence is analyzed initially, and only those variants that are identified in the initial step are utilized for scanning in later grouping processes. The scanning step can utilize a number of technology platforms such as chips, capillary or gel based DNA sequencers, microtiter hybridization wells, beads, fiber optics, or others.

In some embodiments, the entire genetic code in the reference database 130 is analyzed or scanned for variants. In other embodiments, at least the non-repeat regions of the reference database are analyzed to identify variants (e.g., SNPs). In some embodiments, only common variants are identified. Preferably, genic and non-genic regions of the sequences in the database are analyzed. Preferably, more than 1,000,000 bases are analyzed, preferably more than 10,000,000, more preferably more than 100,000,000, more preferably more than 500,000,000, and more preferably more than 1,000,000,000 bases. In some aspects, more than 50% of at least one chromosome is scanned in multiple samples. In other aspects, more than two chromosomes, more than five chromosomes, or all of the chromosomes in the particular organism under study are scanned in multiple samples. By "common" SNPs, it is intended to refer to SNPs occurring in more than 2% of the sample population studied, or more than 4% of the population studied, or more than 6% of the population studied, or more than 8% of the population studied, or more than 10% of the population studied. Of course, rare SNPs can also be selected for use in particular association studies at step 125, which can lead to the commercialization of diagnostics and therapeutics and at step 170. "Rare" SNPs are non-common SNPs. Furthermore, the wafers or arrays used herein may also be used to compare genomes of, e.g. humans with other organisms such as mouse, rat or dog to, e.g. identify conserved regions as step 123 (see, e.g., U.S. patent applications Ser. No. 10/142,364, filed May 8, 2002, entitled "Methods for Nucleic Acid Analysis".) The results from such genome comparisons may be used, e.g., to identify a subspecies of an organism, to study phylogenetic relationships between organisms, or to determine regions of a genome that contain functional elements or sequences, such as genes or regulatory regions.

The SNPs, haplotype blocks and other variant information such as variant DNA stretches can be stored in a database 121, which may be, in whole or in part, licensed directly for revenue. In addition, in one embodiment, common variants identified at step 120 are placed in haplotype blocks and haplotype patterns are identified for each haplotype block. This can be accomplished, for example, using the methods disclosed in U.S. Ser. Nos. 60/280,530, filed Mar. 30, 2001; U.S. Ser. No. 60/313,264, filed Aug. 17, 2001; U.S. Ser. No. 60/327,006, filed Oct. 5, 2001; U.S. Ser. No. 60/332,550, filed Nov. 26, 2001; U.S. Ser. No. 10/106,097, now U.S. Pat. No. 6,969,589, filed Mar. 26, 2002; U.S. Ser. No. 10/284,444, filed Oct. 31, 2002; and U.S. Ser. No. 10/467,558, filed Feb. 14, 2003, previously incorporated herein by reference. Representative variants, haplotype blocks, and haplotype patterns from an entire human chromosome (chromosome 21) are disclosed in, for example, in Patil, N. et al, "Blocks of Limited Haplotype Diversity Revealed by High-Resolution Scanning of Human Chromosome 21" *Science* 294, 1719-1723 (2001) and the associated supplemental materials, incorporated herein by reference. In a related embodiment, SNPs identified are placed in LD bins instead of or in addition to haplotype blocks (see, e.g., Hinds, et al. (2005) "Whole-Genome Patterns of Common DNA Variation in Three Human Populations", *Science* 307:1072-1079.) At step 142, representative SNPs or variant DNA stretches are selected from among the haplotype blocks and/or LD bins to be used in association studies.

The SNPs or variant DNA stretches selected at step 142 may be used in a variety of applications. For example, in collaboration with other companies, one may select portions of the genome of an organism at step 144 that are believed to play a role in a particular phenotype such as a disease state. A partner may or may not provide the funding at step 146 and/or a sample set, for example, of disease and control samples, at step 148. In certain embodiments, funding is used to procure samples from a third party sample source.

At step 150 SNPs, representative SNPs (e.g., informative SNPs) or variant DNA stretches from each sample are used in one or more assays to determine which portions of the tentatively selected functional region correlate or associate in fact with the phenotype of interest. Typically, such SNPs are common SNPs, but rare SNPs may also be selected in step 125. Such assays include, for example, a chip based assay, Invader™ assay, Taqman™ assay, GeneEngine™ sequencer, Pyrosequencing™ assay, MassARRAY™ assay, BeadArray™ assay, or gel or capillary sequencing assay (various of the above being trademarks). An Invader™ assay is based on enzyme-substrate reaction for quantifying DNA and RNA by binding two short DNA probes to a target, enzymatically cleaving the target, binding a fluorescently labeled probe to the cleavage site and then cutting the probe bound DNA to detect a fluorescence signal. A Taqman™ assay is a fluorogenic probe-based assay available from Applied Biosystems (Foster City, Calif.). A GeneEngine™ assay feeds DNA through small channels and then scans the DNA using high-speed optics. A Pyrosequencing™ assay is a sequencing-by-synthesis assay available from Biotage AB (Westborough, Mass.). A MassArray™ assay assembles sequence information using mass spectrometry by obtaining base-specific chain termination information using enzymatic reactions. The BeadArray™ assay utilizes light conducting fiber optic bundle substrates that are composed of 3-micron beads. Other methods that may be used include, for example, molecular inversion probe technology, mismatch repair detection, and TrueTag technology (ParAllele Bioscience, South San Francisco, Calif.), as well as gel and capillary sequencing operations and other assays well known to those skilled in the art.

The funding for use in the business methods herein will normally take on multiple forms. For example, the funding may be by way of funding for costs of performing the particular study in question, in some cases with margin. In addition funding may be provided by way of milestone payments, for example, at the time the SNPs, haplotype blocks and/or haplotype patterns are identified in a region, at the time the association study is completed, at the time research results are confirmed, at the time clinical trials of various stages are started and/or completed, at the time drugs or diagnostics begin to be marketed and/or reach sales milestones, and/or royalties on sales of the relevant drug, diagnostic, or drug sold in conjunction with the population segregation diagnostic, or similar fees for other products such as agricultural products or consumer products. In addition, particular partners may provide funding by way of equity investment, and/or equity may be sold to investors.

Alternatively, or in addition, at step 152 whole genome studies are performed whereby the SNPs or variant DNA stretches from all or a substantial part of the genome, are correlated or associated with a phenotypic state such as a disease state, for example. This correlation/association study may also be conducted through pooling samples to reduce overall costs or by genotyping individual samples. Methods for pooled and individual genotyping are provided, e.g., in U.S. patent application Ser. No. 10/768,788, filed Jan. 30, 2004 and PCT application no. US04/06693, filed Mar. 4, 2004, both of which are entitled "Apparatus and Methods for Analyzing and Characterizing Nucleic Acid Sequences"; U.S. patent application Ser. No. 10/786,475, filed Feb. 24, 2004, entitled "Improvements to Analysis Methods for Individual Genotyping"; and U.S. patent application Ser. No. 10/970,761, filed Oct. 20, 2004, entitled "Improved Analysis Methods and Apparatus for Individual Genotyping". This step may also be performed in collaboration with others, who may provide samples at step 154 and/or funding at step 156. Of course, the sample source and the funding source may or may not be the same in each of the studies herein. In one example, the funding source may be a pharmaceutical company and the source of samples may be a hospital, academic research center or other company. In another example, the funding source and/or sample source may be from an insurance company, government entity or employer.

In one embodiment, at step 197 rights to a drug or product are acquired prior to initiating association studies. Such drug or product may be, for example, one that has been pulled off the market due to unpredictable adverse effects in a small group of individuals or may be one that did not obtain regulatory approval due to a large number of individuals experiencing unanticipated effects in clinical trials. The company may then be able to use association studies to correlate genomic differences and drug responses, and may further use the correlations or associations identified therein to create a diagnostic kit to identify patients who may benefit from the drug. Thus, by stratifying patients and identifying outlier individuals, a company may be able to both obtain regulatory approval and increase drastically the value of its acquired drugs. In other embodiments, rights to a drug or product are acquired during or subsequent to one or more association studies. In certain embodiments, rights to a drug or products are sought after review of the results of one or more association studies. For example, it may be found that a particular gene, RNA or protein is found to be associated with a given disease, and the company may seek rights to a drug or product known to target the associated gene, RNA or protein.

A number of activities can be based upon the results of steps 150 and 152. For example, at step 158 diagnostic markers may be used to develop diagnostic tests, e.g., that are indicative of a patient's tendency to a disease (or, for example, being a carrier of a disease variant), an individual's resistance to a disease, or a patient's drug response profile. Based on the markers, the diagnostics may be developed and commercialized at step 160. The diagnostics may take on a number of forms such as immunoassays, chip based DNA assays, PCR assays, Taqman™ assays, sequencing based assays or the like.

In addition, or in the alternative, at step 162 the correlation studies are used to select disease targets for drug development. Once a genetic locus or multiple loci in the genome are associated with a particular phenotypic trait, for example, a disease susceptibility locus, the gene(s) or regulatory element(s) responsible for the trait can be identified. These gene(s) or regulatory element(s) may then be used as therapeutic targets for the treatment of the disease, as shown at step 164, or for commercialization, as shown at step 166, independently or in collaboration with partners.

In addition, or in the alternative, at step 168 the phenotypic trait of drug response is used to stratify patients into various groups. The groups may be, for example, those that respond to a drug versus those that do not respond, those that respond to a drug without toxic or otherwise adverse effects, versus those that are observed to have toxic or otherwise adverse effects. At step 170 the therapeutic may be marketed with an associated diagnostic that is capable of segregating those that will respond to the drug in an acceptable manner from those that will not.

Figure 2:
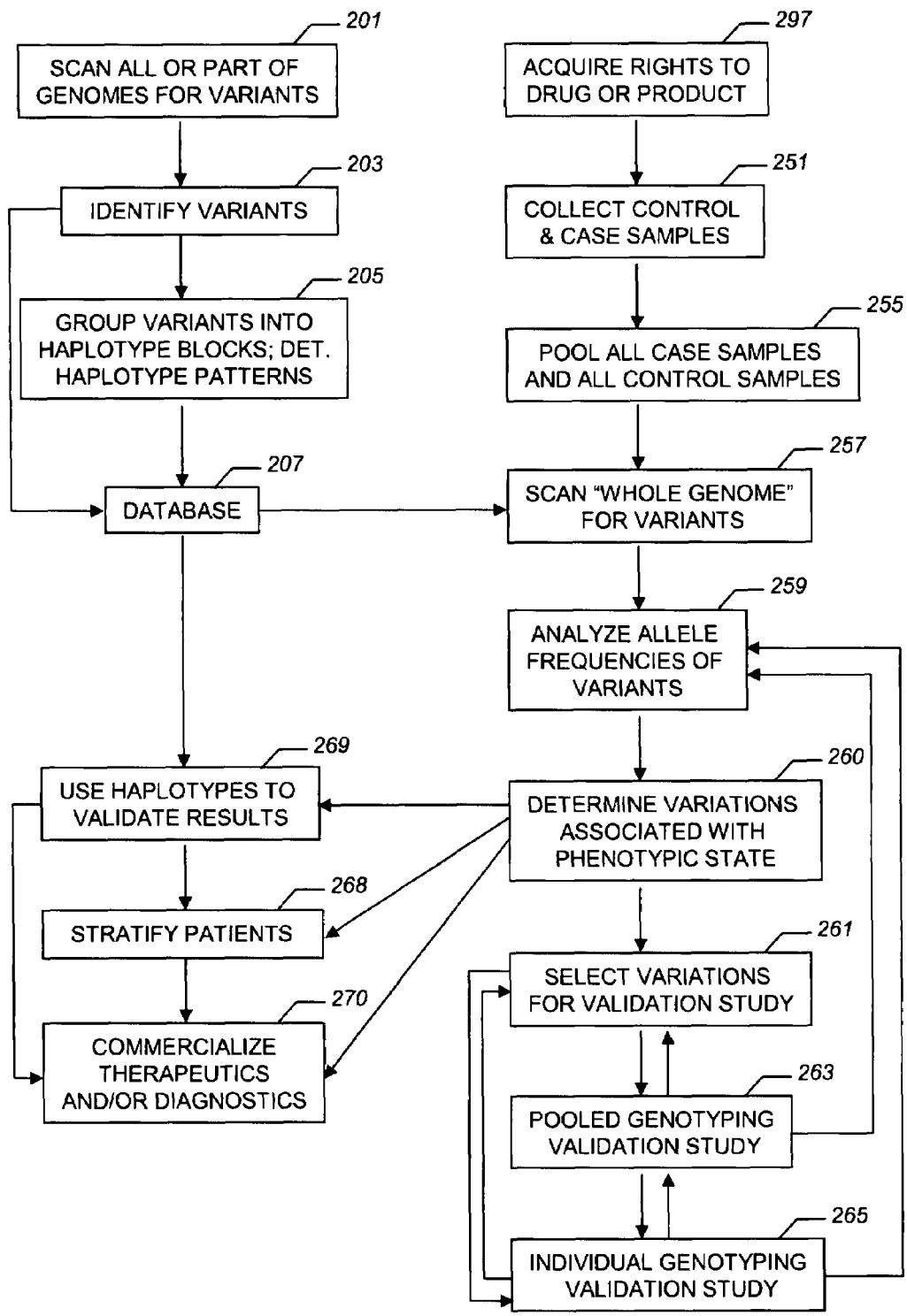
FIG. 2 is a flow chart illustrating certain aspects of the business method herein.

FIG. 2 illustrates another embodiment of the methods and systems herein. At step 201, a plurality of whole genomes is scanned to identify variants. Table II, row 1 below, illustrates a contiguous stretch of genomic DNA with all identified variants from two individuals. (In the interest of simplicity, although the individuals may be diploid only one DNA strand is shown for each.) The sequences for "individual 1 " and "individual 2 " are incorporated herein by reference. At this stage, the variants may include common SNPs, rare SNPs and variant DNA stretches. In this example, each variant is a SNP and is illustrated by a framed base.

Next at step 203, genetic variants (e.g., SNPs) and the genetic sequences in which they lie are identified, and at step 205 variants (e.g., common SNPs) are grouped into haplotype blocks and haplotype patterns are determined using any one or more of the methods herein. The variants, haplotype blocks and haplotype patterns are stored in a database at step 207. Table II, row 2, illustrates common SNPs grouped into three haplotype blocks. Starting from the left of the genomic sequence, nucleotide positions illustrated in bold font (C, T, A in individual 1 and the T, C and G in individual 2) comprise a first haplotype block; next, nucleotides positions illustrated in underlined font (C, C, A in individual 1 and A, T, and G in individual 2) comprise a second haplotype block; furthermore, nucleotide positions illustrated in bold and italic font (T and C in individual 1 and G and G in individual 2) comprise a third haplotype block. Haplotype patterns are also identified for each haplotype block. In Table II, row 2, for each haplotype block, individual 1 has a different haplotype pattern than individual 2 (e.g., "C-T-A" vs. "T-C-G", "C-C-A" vs. "A-T-G", and "T-C" vs. "G-G"). These common SNPs, haplotype blocks and haplotype patterns can be used in association studies as described below.

TABLE II

1  Scan whole genomes to identify variants:

[C]GA[T]CTG[A]GCG[C]CC[C]TT[A]AC[T]T[C] (individual 1)

[T]GA[C]CTG[G]GCG[A]CC[T]TT[G]AC[G]T[G] (individual 2)

2  Identify common variants, group them into haplotype blocks, and identify haplotype patterns:

[C]GA[T]CTG[A]GCG[C]CC[C]TT[A]AC[T]T[C] (individual 1)

[T]GA[C]CTG[G]GCG[A]CC[T]TT[G]AC[G]T[G] (individual 2)

The variants and their haplotype patterns are used in association studies to correlate genomic regions with a phenotypic state of interest that distinguishes a case group (a population of individuals that exhibit the phenotypic state of interest) from a control group (a population of individuals that do not exhibit the phenotypic state of interest). A set of variants is chosen for use in an association study. In the embodiment depicted in FIG. 2, variants are chosen from a database that contains variants identified in a genome scan. In some embodiments, the variants chosen are common SNPs; in other embodiments, the variants chosen are informative or representative SNPs based on haplotype blocks/patterns and/or on linkage disequilibrium analysis (e.g., LD bins). In certain embodiments, variants from across the genome are chosen, and in other embodiments, variants from regions of the genome believed to contain loci associated with the phenotypic state ("candidate regions") are chosen. Variants may be chosen from genic or nongenic regions, and may encode synonymous changes, nonsynonymous changes, or no changes at all in a gene product. For a description and examples of nonsynonymous SNPs in the human genome and uses thereof, see e.g., U.S. patent application Ser. No. 60/572, 533, filed May 18, 2004. At least about 100, 500, 1000, 10,000, 50,000, 100,000, 250,000, 500,000, 1,000,000, 3,000,000, 5,000,000 or 10,000,000 variants may be chosen.

Samples containing nucleic acids (e.g., genomic DNA) are collected from each individual in each of the case and control groups at step 251. In the embodiment depicted in FIG. 2, a pooled genotyping methodology is utilized as a first round of an association study. After case and control samples containing nucleic acids are obtained at step 251 all control samples and all case samples are "pooled" together at step 255 to create a "control pool" and a "case pool". In certain embodiments, the control samples and case samples are purified nucleic acid samples. The pooled samples are scanned (i.e., genotyped) at step 257, and a measure of the allelic constitution for the variants in the case and control pools is computed at step 259 using any of the methods herein. In some embodiments only common variants are analyzed, but in other embodiments variants may be chosen based on other criteria, as described below. Methods for pooled genotyping are described in detail in U.S. patent application Ser. No. 10/768,788, filed Jan. 30, 2004 and PCT application no. US04/06693, filed Mar. 4, 2004, both of which are entitled "Apparatus and Methods for Analyzing and Characterizing Nucleic Acid Sequences."

In certain embodiments of the present invention, individual genotyping may be performed in a first round of an association study. Individual genotyping comprises evaluating the genotype of each individual for each variant position. The abundance of each allele for each variant is determined and those variants that have allele frequencies that are significantly different in the case group than in the control group are identified as associated with the phenotypic state of interest that distinguishes the case group from the control group. Methods for individual genotyping are described in detail in U.S. patent application Ser. No. 10/786,475, filed Feb. 24, 2004, entitled "Improvements to Analysis Methods for Individual Genotyping"; and U.S. patent application Ser. No. 10/970,761, filed Oct. 20, 2004, entitled "Improved Analysis Methods and Apparatus for Individual Genotyping."

After genotyping the cases and controls the relative allele frequencies of variants (in some embodiments, only common variants) are computed and analyzed at step 259. For each variant, the allele frequency in the case group is compared to that in the control group to determine which variants are associated with the phenotypic state of interest at step 260. Pooled genotyping is often used during a first round of an association study. Most often, only some of the variants will be found to correlate or associate with a phenotypic state. However, at this stage, even variants that show a relatively low degree of correlation are retained for further analysis. If the relative allele frequency of a variant in the case group is substantially the same in the control group, (i.e., when a SNP allele appears in approximately the same abundance in the case samples as it does in the control samples), the variant is determined not to be associated with the phenotype that distinguishes the case group from the control group and may be excluded from further analysis. On the other hand, if the relative allele frequency of a variant in the case group is not substantially similar to its relative allele frequency in the control group, the variant is determined to be associated with the phenotypic state of interest that differentiates the case group from the control group. Further, the alleles and haplotype patterns that are more common in the case group are determined to be associated with the presence of the phenotypic state of interest, and the alleles and haplotype patterns that are more common in the control group are determined to be associated with the absence of the phenotypic state of interest. Thus, these alleles and haplotype patterns may be used to determine whether an individual of unknown phenotype is likely to exhibit the phenotypic state of interest (e.g., disease susceptibility or resistance, efficacious drug response, or likelihood of experiencing an adverse event in response to a medical treatment), as described herein.

As described above, association studies may comprise multiple stages or "rounds" of analysis. In some embodiments, an association study comprises a combination of one or more pooled genotyping stages/rounds and individual genotyping stages/rounds. For example, the variants (including their associated genomic regions, haplotype blocks and haplotype patterns) correlated in a first round of an association study can be validated by one or more additional rounds of the association study, sometimes referred to as "validation studies", at step 263 or 265. In general, a validation study comprises analyzing a subset of variants that were previously analyzed in an earlier stage of the associations study, for example, reanalyzing those variants (including their associated genomic regions, haplotype blocks and haplotype patterns) that were found to be associated with the phenotypic state of interest in one round (e.g., the first round) of an association study to determine whether they "replicate" in an additional round of the association study. For example, those variants (including their associated genomic regions, haplotype blocks and haplotype patterns) that are identified as associated with the phenotypic state of interest in the first round of the association study and in the one or more validation studies are thereby validated as associated with the phenotypic state of interest. In certain embodiments, however, additional variants may also be selected for screening in a validation study such as, for example, those in genomic regions believed to contain loci associated with the phenotypic state based on additional studies (e.g., inheritance patterns, etc.) For example, a first stage may comprise a pooled genotyping methodology to screen a very large number of variants (e.g., at least about 1,000,000), and the variants that are identified as associated are selected at step 261 and are subjected to a further screening using a pooled genotyping methodology at step 263 or an individual genotyping methodology at step 265. The same or different case and control populations may be used for each stage. For example, a second case group and a second control group may be used in later stages of an association study in order to validate the associated variants found using a first case group and a first control group, as described further below.

A plurality of pooled and/or individual genotyping stages may be used in a single multistage association study. As shown in FIG. 2, a first round of an association study may be followed by a pooled genotyping validation study at step 263 or an individual genotyping validation study at step 265. Variations used for a pooled genotyping verification study at step 263 may be subsequently used in an individual genotyping validation study at step 265, and vice versa. Alternatively, only those variations identified as associated (i.e., validated) in a pooled or individual genotyping are chosen for further validation studies at step 261. In certain embodiments, a verification study comprises rescanning the case and control pools and reanalyzing the relative allele frequencies for each variant in each pool. In certain embodiments, a verification study comprises scanning a second case pool and a second control pool for the associated variants (including their associated genomic regions, haplotype blocks and haplotype patterns) identified in a previous round of an association study, wherein the second case and control pools are derived from a second case group and a second control group, respectively. In certain embodiments, a verification study comprises genotyping individual samples to determine actual allele frequencies for the case and control group from a previous round of an association study in which a pooled genotyping methodology was used. In certain embodiments, a verification study comprises genotyping individual samples to determine actual allele frequencies for a second case group and a second control group that are distinct from the case and control groups from a previous round of an association study. In some embodiments, combinations of validation studies are performed. For example, a pooled genotyping validation study that uses the same case and control pools as the first round of an association study may be followed by 1) a pooled genotyping validation study that uses the same case and control pools, 2) a pooled genotyping validation study that uses a different case pool and a different control pool, 3) an individual genotyping validation study that uses the same case and control groups as was used in the first round of the association study, 4) an individual genotyping validation study that uses a different case group and a different control group, or 5) a combination thereof. In other embodiments, a pooled genotyping validation study that uses a different case pool and a different control pool than a previous round of an association study may be followed by one or more individual genotyping validation studies, which may use either the same or different case and control groups as the previous round of the association study. In yet other embodiments, an individual genotyping validation study using given case and control groups may be followed by an additional individual genotyping validation study that uses different case and control groups. Further examples of association study design are provided, e.g., in U.S. patent application Ser. Nos. 10/106,097, filed Mar. 26, 2002, now U.S. Pat. No. 6,969,589; 10/042,819, filed Jan. 7, 2002, now U.S. Pat. No. 6,897,025; 10/286,417, filed Oct. 31, 2002; 60/648,957, filed Jan. 31, 2005; 10/447,685, filed May 28, 2003; 10/691,069, filed Oct. 21, 2003; 10/427,696, filed Apr. 30, 2003, now U.S. Pat. No. 7,124,033; 60/572,533, filed May 18, 2004; 10/845,316, filed May 12, 2004; 10/940,410, filed Sep. 13, 2004; 11/043,689, filed Jan. 24, 2005; 10/956,224, filed Sep. 30, 2004, now U.S. Pat. No. 7,127,355; and 60/643,006, filed Jan. 11, 2005; as well as PCT application No. US04/016950, filed May 27, 2004; US04/13577, filed Apr. 30, 2004; and US05/07375, filed Mar. 3, 2005.

In addition to genotyping individual samples, the haplotype blocks and patterns identified at step 205 can also be used to verify highly correlated variants or variant DNA stretches from the first round of an association study at step 269. In particular, after genotyping a sample for highly correlated variants, haplotype blocks can be used to verify genotyping results. For example, referring again to Table II, the haplotype pattern for the leftmost haplotype block in individual 1 is C-T-A and the haplotype pattern for the same haplotype block in individual 2 is T-C-G. If the "C" allele at the first variant position in the haplotype block is found to be associated with a phenotypic state of interest, then the "T" in the second variant position and the "A" in the third variant position would also be expected to be associated due to the linkage disequilibrium between these three variant positions. Thus, if an association study identifies as associated a set of alleles that are part of a single haplotype pattern, the confidence in the validity of that association is reinforced.

The results obtained from steps 260, 263, 265, and 269 can be used for one or more of the applications previously described herein, for example, the development of diagnostic markers, kits and reagents for identifying a phenotypic trait of interest at step 270, the identification of target genomic regions for drug discovery at step 270, or stratification of patient populations at step 268, for example. Any of these applications can be accomplished independently or in collaboration with partners.

The genomic sequences identified by the methods of the present invention may be genic or nongenic sequences. The term "identified gene" is intended to mean the open reading frame encoding specific RNAs, polypeptides, intronic regions, generally, as well as adjacent 5' and 3' non-coding nucleotide sequences involved in the regulation of expression of the gene up to about 10 kb beyond the coding region, but possibly further in either direction of a gene identified in an association study. The coding sequences (ORFS) of an identified gene may affect a phenotypic state by affecting the structure or activity of an encoded protein or RNA (e.g., binding affinity, ribozyme/enzyme kinetics, etc.). Alternatively, the non-coding sequences of the identified gene or nongenic sequences may affect a phenotype state by impacting the level of expression or specificity of expression of a protein or RNA product.

Genomic sequences are studied generally by isolating the identified genomic sequence such that it is substantially free of other nucleic acid sequences that do not include the sequence of interest. The sequences are used in a variety of ways. For example, the nucleic acid sequence may be used to detect or quantify expression of a gene in a biological specimen. The manner in which one probes cells for the presence of particular nucleotide sequences is well established in the literature and does not require elaboration here, see, e.g., Sambrook, et al., *Molecular Cloning: A Laboratory Manual* (Cold Spring Harbor Laboratory, New York) (1989).

Alternatively, individuals may be studied that are resistant to a particular disease, such as HIV. By understanding the genetic basis of disease resistance it may be possible to identify therapeutic and/or diagnostic targets. In addition, individuals may be selected for desirable traits such as, for example, healthy state, enhanced performance state, protective state, extended longevity and resistance state.

According to one aspect of the business systems and methods disclosed herein, when a region of the genome has been identified as playing a role in a phenotypic state, after a first, second or any subsequent rounds of association studies (e.g., validation studies), the genome may be the subject of further SNP scanning at steps 120, 260, 263 or 265, for example to identify rare SNPs that may be associated with a disease. For example, such further scanning may comprise sequence analysis to identify rare SNPs and/or SNP genotyping to determine the association of rare SNPs with the phenotypic state based on the rare SNP genotypes in case and control individuals. In addition, such further scanning may involve scanning the entire genome, or only a portion thereof (e.g., regions containing common SNPs found to be associated, candidate regions based on clinical studies, etc.). These SNPs may play a role in, for example, rare forms of the disease.

In addition, the sequence of the gene (including flanking promoter regions and coding regions) may be mutated in various ways known in the art to generate targeted changes in promoter strength, or changes in the sequence of the encoded protein, etc. The sequence changes may be, e.g., substitutions, translocations, insertions or deletions. Deletions may further include larger changes, such as deletions of a domain or exon. Techniques for in vitro mutagenesis of cloned genes are known. Examples of protocols for site-specific mutagenesis may be found in Gustin, et al., *Biotechniques* 14:22 (1993); Barany, *Gene* 37:111-23 (1985); Colicelli, et al., *Mol. Gen. Genet.* 199:537-9 (1985); Prentki, et al., *Gene* 29:303-13 (1984); Sambrook, et al., *Molecular Cloning: A Laboratory Manual* (Cold Spring Harbor Press) pp. 15.3-15.108 (1989); Weiner, et al., *Gene* 126:35-41 (1993); Sayers, et al., *Biotechniques* 13:592-6 (1992); Jones and Winistorfer, *Biotechniques* 12:528-30 (1992); and Barton, et al.,o Nucleic Acids Res. 18:7349-55 (1990). Such mutated genes may be used to study structure/function relationships of the protein product, or to alter the properties of the protein that affect its function or regulation.

An associated gene identified by the methods presented herein may be employed for producing all or portions of the resulting RNA, polypeptide, or protein. To express an RNA or protein product, an expression cassette incorporating the identified gene may be employed. The expression cassette or vector generally provides a transcriptional and translational initiation region, which may be inducible or constitutive, where the coding region is operably linked under the transcriptional control of the transcriptional initiation region, and a transcriptional and translational termination region. These control regions may be native to the identified gene, or may be derived from exogenous sources.

The RNA or polypeptide may be expressed in prokaryotes or eukaryotes in accordance with conventional methods, depending upon the purpose for expression. For large-scale production of the RNA or protein, a unicellular organism, such as *E. coli, B. subtilis, S. cerevisiae,* insect cells in combination with baculovirus vectors, or cells of a higher organism such as vertebrates, particularly mammals, e.g. COS 7 cells, may be used as the expression host cells. In many situations, it may be desirable to express the gene in eukaryotic cells, where the gene product will benefit from native folding and post-translational modifications. Small RNAs and peptides also can be synthesized in the laboratory. With the availability of the RNA, protein, or fragments thereof in large amounts, the RNA or protein may be isolated and purified in accordance with conventional ways. A lysate may be prepared of the expression host and the RNA or protein purified using HPLC, exclusion chromatography, gel electrophoresis, affinity chromatography, or other purification technique.

An expressed protein may be used for the production of antibodies, where short fragments induce the expression of antibodies specific for the particular polypeptide, and larger fragments or the entire protein allow for the production of antibodies over the surface of the polypeptide (polyclonal antibodies). Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes are immortalized by cell fusion and screened for high affinity antibody binding. The immortalized cells, e.g., hybridomas, producing the desired antibodies may then be expanded. For further description, see *Monoclonal Antibodies: A Laboratory Manual,* Harlow and Lane, eds. (Cold Spring Harbor Laboratories, Cold Spring Harbor, N.Y.) (1988). If desired, the mRNA encoding the heavy and light chains may be isolated and mutagenized by cloning in *E. coli,* and the heavy and light chains mixed to further enhance the affinity of the antibody. Alternatives to in vivo immunization as a method of raising antibodies include binding to phage "display" libraries, usually in conjunction with in vitro affinity maturation.

The identified genes, gene fragments, or the encoded RNA, protein or fragments thereof may be useful in gene therapy to treat degenerative and other disorders. For example, expression vectors may be used to introduce the identified gene (or variant thereof) into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to be transiently or stably maintained in the cells. The gene or protein product may be introduced into tissues or host cells by any number of routes, including viral infection, microinjection, or fusion of vesicles. Jet injection may also be used for intramuscular administration, as described by Furth, et al., *Anal. Biochem,* 205:365-68 (1992). Alternatively, the DNA may be coated onto gold microparticles, and delivered intradermally by a particle bombardment device, or "gene gun" as described in the literature (see, for example, Tang, et al., *Nature,* 356:152-54 (1992)).

Antisense molecules can be used to down-regulate expression of the identified gene in cells. The antisense reagent may be antisense oligonucleotides, particularly synthetic antisense oligonucleotides having chemical modifications, or nucleic acid constructs that express such antisense molecules as RNA. The antisense sequence may be complementary to the mRNA of the targeted gene, and inhibits expression of the targeted gene products. Antisense molecules inhibit gene expression through various mechanisms, e.g., by reducing the amount of mRNA available for translation, through activation of RNAse H, or by steric hindrance. One or a combination of antisense molecules may be administered, where a combination may comprise multiple different sequences.

As an alternative to antisense inhibitors, catalytic nucleic acid compounds, e.g., ribozymes, anti-sense conjugates, RNA interference, etc., may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman, et al., *Nucl. Acids Res.* 23:4434-42 (1995)). Examples of oligonucleotides with catalytic activity are described in WO 9506764. Conjugates of antisense oligonucleotides with a metal complex, e.g. terpyridylCu(II), capable of mediating mRNA hydrolysis are described in Bashkin, et al., *Appl. Biochem. Biotechnol.* 54:43-56 (1995). RNAi, or "RNA interference" is a technique in which exogenous, double-stranded RNA complementary to a known target mRNA are introduced into a cell to cause the degradation of the target mRNA, thereby reducing or silencing gene expression. This method of gene regulation has been demonstrated in *Drosophila, Coenorhabditis elegans,* plants, and in mammalian cell cultures. In mammalian cells, siRNAs ("small-interfering RNAs" that are double-stranded) are transfected into cells. siRNAs can be created using a phage enzyme known as "DICER" and a multi-protein siRNA complex termed "RISC" (RNA induced silencing complex). Briefly, duplexes of short (~19 nucleotides in length) RNAs with symmetric 2-nucleotide 3'-overhangs (siRNAs) are introduced into a cell where they associate with specific proteins in a ribonucleoprotein complex, which scans the mRNA in the cell and degrades the mRNA target that is homologous to the siRNA, thereby preventing translation of the mRNA message and, therefore, synthesis of the protein encoded therein. For a review of RNAi techniques, see, e.g., Huppi, et al. (2005) "Defining and Assaying RNAi in Mammalian Cells", *Molecular Cell* 17(1):1-10; Grimm, et al. (2005) "Adeno-associated virus vectors for short hairpin RNA expression", *Methods Enzymol* 392:381-405; Bantounas, et al. (2004) "RNA interference and the use of small interfering RNA to study gene function in mammalian systems". *J Molec Endocrin* 33:545-557; Genc, et al. (2004) "RNA interference in neuroscience", *Brain Res Mol Brain Res* 132(2):260-270; and Campbell, et al. (2005) "RNA interference: past, present and future", *Curr Issues Mol Biol* 7(1):1-6.

In addition to using the identified sequences for gene therapy, the identified nucleic acids can be used to generate genetically modified non-human animals to create animal models of diseases or to generate site-specific gene modifications in cell lines for the study of protein function or regulation. The term "transgenic" is intended to encompass genetically modified animals having an exogenous gene that is stably transmitted in the host cells where the gene may be altered in sequence to produce a modified protein, or having an exogenous promoter operably linked to a reporter gene. Transgenic animals may be made through homologous recombination, where the gene locus is altered. Alternatively, a nucleic acid construct is randomly integrated into the genome. Vectors for stable integration include plasmids, retroviruses and other animal viruses, YACs, and the like. Of interest are transgenic mammals, e.g., cows, pigs, goats, horses, etc., and, particularly, rodents, e.g., rats, mice, etc.

Investigation of genetic function may also utilize non-mammalian models, particularly using those organisms that are biologically and genetically well-characterized, such as *C. elegans, D. melanogaster* and *S. cerevisiae*. The subject gene sequences may be used to knock-out corresponding gene function or to complement defined genetic lesions in order to determine the physiological and biochemical pathways involved in protein function. Drug screening may be performed in combination with complementation or knock-out studies, e.g., to study progression of degenerative disease, to test therapies, or for drug discovery.

In addition, the modified cells or animals are useful in the study of RNA and protein function and regulation. For example, a series of small deletions and/or substitutions may be made in an identified gene to determine the role of different domains in enzymatic activity, cell transport or localization, etc. Specific constructs of interest include, but are not limited to, antisense constructs to block gene expression, expression of dominant negative genetic mutations, and over-expression of the identified gene. One may also provide for expression of the identified gene or variants thereof in cells or tissues where it is not normally expressed or at abnormal times of development. Furthermore, by providing expression of an RNA or protein in cells in which it is otherwise not normally produced, one can induce changes in cellular behavior.

RNA or protein molecules may be assayed to investigate structure/function parameters. For example, by providing for the production of large amounts of an RNA or protein product of an identified gene, one can identify ligands or substrates that bind to, modulate or mimic the action of that RNA or protein product. Drug screening identifies agents that provide, e.g., a replacement or enhancement for RNA or protein function in affected cells or for agents that modulate or negate RNA or protein function. The term "agent" as used herein describes any molecule, e.g. nucleic acid, protein or small molecule, with the capability of altering or mimicking the physiological function of an identified gene, gene regulatory region or gene product. Generally a plurality of assays is run in parallel with different agent concentrations to obtain a differential response to the various concentrations. Typically, one of these concentrations serves as a negative control, e.g., at zero concentration or below the level of detection.

A wide variety of assays may be used for this purpose, including labeled in vitro protein-protein binding assays, protein-DNA binding assays, RNA-DNA binding assays, RNA-protein binding assays, electrophoretic mobility shift assays, immunoassays for RNA or protein binding, gene expression assays and the like. Also, all or a fragment of a purified RNA or protein may also be used for determination of three-dimensional crystal structure, which can be used for modeling intermolecular interactions, membrane fusion, etc.

Candidate agents encompass numerous chemical classes, though typically they are organic molecules, preferably small organic molecules, having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, and frequently at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, benzodiazapines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g., magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc may be used.

Agents, including any other compound or molecule disclosed, may be combined with a pharmaceutically acceptable carrier. Pharmaceutical carriers include, for example, any and all solvents, dispersion media, coatings, anti-oxidant, isotonic and absorption delaying agents and the like. The use of such carriers and agents in pharmaceutical compounds is well known in the art. Except insofar as any conventional carrier or agent is incompatible with the active ingredient, its use in the therapeutic compositions and methods described herein is contemplated. Supplementary active ingredients can also be incorporated into the pharmaceutical compounds disclosed.

Formulation of pharmaceutical compounds may be prepared for use in various methods for administration. The formulation may be given orally, by inhalation, or may be injected, e.g. intravascular, intratumor, subcutaneous, intraperitoneal, intramuscular, etc. The dosage of the therapeutic formulation will vary widely, depending upon the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc., to maintain an effective dosage level. In some cases, oral administration will require a higher dose than if administered intravenously. Identified agents of the invention can be incorporated into a variety of formulations for therapeutic administration. More particularly, the complexes can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the agents can be achieved in various ways. Agents may be systemic after administration or may be localized by the use of an implant that acts to retain the active dose at the site of implantation.

For oral preparations, an agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Additionally, agents may be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Further, agents may be utilized in aerosol formulation to be administered via inhalation. The compounds of the present invention can be formulated into pressurized acceptable propellants such as dichlorodifluoromethane, propane, nitrogen and the like. Furthermore, agents may be made into suppositories by mixing with a variety of bases such as emulsifying bases or water-soluble bases. Alternatively, identified agents of the present invention can be administered rectally via a suppository. The suppository can include vehicles such as cocoa butter, carbowaxes and polyethylene glycols, which melt at body temperature, yet are solid at room temperature.

Implants for sustained release formulations are well known in the art. Implants are formulated as microspheres, slabs, etc. with biodegradable or non-biodegradable polymers. For example, polymers of lactic acid and/or glycolic acid form an erodible polymer that is well tolerated by the host. The implant containing identified agents of the present invention may be placed in proximity to the site of action, so that the local concentration of active agent is increased relative to the rest of the body. Unit dosage forms for oral or rectal administration such as syrups, elixirs, and suspensions may be provided wherein each dosage unit, for example, teaspoonful, tablespoonful, gel capsule, tablet or suppository, contains a predetermined amount of the compositions of the present invention. Similarly, unit dosage forms for injection or intravenous administration may comprise the compound of the present invention in a composition as a solution in sterile water, normal saline or another pharmaceutically acceptable carrier. The specifications for the novel unit dosage forms of the present invention depend on the particular compound employed and the effect to be achieved, and the pharmacodynamics associated with each active agent in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

A therapeutic dose of an identified agent is administered to a host suffering from a disease or disorder. Administration may be topical, localized or systemic, depending on the specific disease. The compounds are administered at an effective dosage that over a suitable period of time substantially arrests the disease progression. It is contemplated that the composition will be obtained and used under the guidance of a physician for in vivo use.

The dose will vary depending on the specific agent and formulation utilized, type of disorder, patient status, etc., at a dose sufficient to address the disease or symptoms thereof, while minimizing side effects. Treatment may be for short periods of time, e.g., after trauma, or for extended periods of time, e.g., in the prevention or treatment of schizophrenia.

In addition or in the alternative, at steps 168 and 268, the phenotypic trait of drug response is used to stratify, or segregate, patients into various groups. The groups may be, for example, those that respond to a drug versus those that do not respond, those that respond to a drug without toxic effects, versus those that are observed to have toxic effects. At steps 170 and 270, the therapeutic may be marketed with an associated diagnostic that is capable of segregating those that will respond in an acceptable manner to the drug from those that do not. In a preferable embodiment, the rights to such drugs or other products are acquired in step 197 or 297, in some embodiments prior to demonstration of ability to genetically stratify patients. Those rights, as well as the value-added genetic information on how to stratify patients, can then be licensed to a third-party for milestone payments and/or royalties. The drug or other products (with or without the related diagnostic kit) can also be commercialized independently or with partner(s) in order to generate product sales.

According to one aspect of the invention herein, the technology platform used for one or more of the scanning steps 120, 201, 257, 263, 265 and/or the correlation steps 150, 152, 259, 260, 263, 265 and 269 are made available at a low or discounted price to the organization conducting the research discussed herein, preferably exclusively for at least a period of time in a specified field. In return the technology provider receives from the business organization discussed herein one or more of equity, royalties on discoveries, licenses to the content generated in one or more of steps 120, 150, 152, 201, 257, 259, 260, 263, 265 and 269 in a selected field and/or improvements to the technology platform, such as improvements made to chip technology. In an alternative embodiment, the organization conducting the research discussed herein is formed as a "tracking stock" of the technology provider. In preferred embodiments, the technology provider does not maintain control (as defined by the relevant accounting standard) of the organization performing the business methods elsewhere discussed herein. In this aspect of the invention, the early financial losses of the research organization need not be consolidated with the technology provider.

It is to be understood that the above description is intended to be illustrative and not restrictive. The scope of the invention should, therefore, be determined not with reference to the above description, but instead with reference to the appended claims along with the full scope of equivalents thereto.

What is claimed is:

1. A business method for obtaining regulatory review of a drug comprising:
   a) genotyping genetic variations in a plurality of individuals;
   b) identifying at least one of said genetic variations that is in linkage disequilibrium with at least one other of said genetic variations;
   c) determining an association between said one of said genetic variations that is in linkage disequilibrium with at least one other of said genetic variations and a response to said drug;
   d) using results from step c to determine whether a patient would benefit from administration of said drug; and
   e) combining information from prior regulatory filings for said drug in combination with information from said association to support a new drug approval regulatory filing.

2. The business method of claim 1 wherein said prior regulatory filings were filed in the United States.

3. The business method of claim 1 wherein said prior regulatory filings were filed in a country outside of the United States.

4. The business method of claim 1, further comprising marketing said drug with a diagnostic test, wherein said diagnostic test stratifies a patient population that displays characteristics that support a treatment regimen with said drug, and further wherein said diagnostic test stratifies said patient population so that a subset of said patient population that is likely to benefit from treatment with said drug is identified.

5. The business method of claim 4 wherein said characteristics comprise at least one of the following: personal medical history, family medical history, or phenotype.

6. The business method of claim 4 wherein said subset of said population contains individuals for whom results from said diagnostic test predict no adverse event if treated with said drug.

7. The business method of claim 4 wherein said subset of said population contains individuals for whom results from said diagnostic test predict an efficacious response if treated with said drug.

8. The business method of claim 1 wherein said plurality of individuals and said patient are human.

9. The business method of claim 1, wherein said determining an association is performed using at least 600 nucleic acid samples, a first portion of which are from patients that benefited from treatment with said drug and a second portion of which are from patients that did not benefit from treatment with said drug.

10. The business method of claim 1, further comprising the step of collecting royalties from sales of said drug.

11. The business method of claim 1 wherein said determining an association is performed without a prior hypothesis that a particular genetic region is associated with said response to said drug.

12. The business method claim 1, wherein said determining an association comprises one or more assays selected from the group consisting of chip-based assays, bead-based assays, sequencing assays, gel assays, capillary sequencing assays, pyrosequencing assays, fluorescent assays, nuclease assays, mass spectrometry assays, enzymatic assays, fiber optic assays, inversion probe assays. and mismatch repair assays.

13. The business method claim 1, wherein at least 10,000 SNPs are evaluated in step (c).

14. The business method of claim 1, further comprising collaboration with a partner, wherein said partner provides at least one of the group consisting of said prior regulatory filings, said drug, genetic samples from said plurality of individuals, and funding.

15. The business method of claim 1, wherein step (c) further comprises sequence analysis of a genomic region containing said one of said genetic variations, wherein said sequence analysis identifies rare SNPs in said genomic region that are associated with said response to said drug.

16. A business method comprising:
   a) genotyping genetic variations in a plurality of individuals;
   b) identifying at least one of said genetic variations that is in linkage disequilibrium with at least one other of said genetic variations;
   c) attaining an in-licensed drug;
   d) reformulating said in-licensed drug to produce a reformulated drug, wherein said reformulated drug has a formulation different from said in-licensed drug's formulation;

e) determining an association between said one of said genetic variations that is in linkage disequilibrium with at least one other of said genetic variations and a response to said reformulated drug; and f) using results from step c to determine whether a patient would benefit from treatment with said reformulated drug.

17. The business method of claim 16 wherein said reformulated drug has an enantiomeric purity that is different from said in-licensed drug's enantiomeric purity.

18. The business method of claim 16 wherein said reformulated drug has a delivery method that is different from said in-licensed drug's delivery method.

19. The business method of claim 18 wherein said delivery method of said reformulated drug is selected from the group consisting of injection, oral administration, implantation, inhalation, insertion and topical application.

20. The business method of claim 16 wherein said reformulated drug has a dosage form that is different from said in-licensed drug's dosage form.

21. The business method of claim 20 wherein said dosage form of said reformulated drug is selected from the group consisting of a tablet, a capsule, a powder, a granule, an ointment, a solution, a suspension, a patch, a suppository, an injection, an inhalant, an aerosol, a gel. and a microsphere.

22. The business method of claim 20 wherein said dosage form of said reformulated drug contains an amount of one or more active ingredients that is different from an amount of said one or more active ingredients contained in said in-licensed drug.

23. The business method of claim 16, further comprising marketing said reformulated drug with a diagnostic test, wherein said diagnostic test stratifies a patient population that has or is at risk of developing a condition or disease that is treatable with said reformulated drug, and further wherein said diagnostic test stratifies said patient population so that a subset of said patient population is identified by said diagnostic test, wherein said subset is predicted to have one or more responses selected from the group consisting of an efficacious response and a lack of an adverse event if treated with said reformulated drug.

24. The business method of claim 16 wherein said determining an association is performed using at least 600 nucleic acid samples, a first portion of which are from patients that had one or more responses selected from the group consisting of an efficacious response and a lack of an adverse event if treated with said reformulated drug; and a second portion of which are from patients that did not have one or more responses selected from the group consisting of an efficacious response and a lack of an adverse event if treated with said reformulated drug.

25. The business method of claim 16 wherein said determining an association is performed without a prior hypothesis that a particular genetic region is associated with said response to said reformulated drug.

* * * * *